Figure 1A:
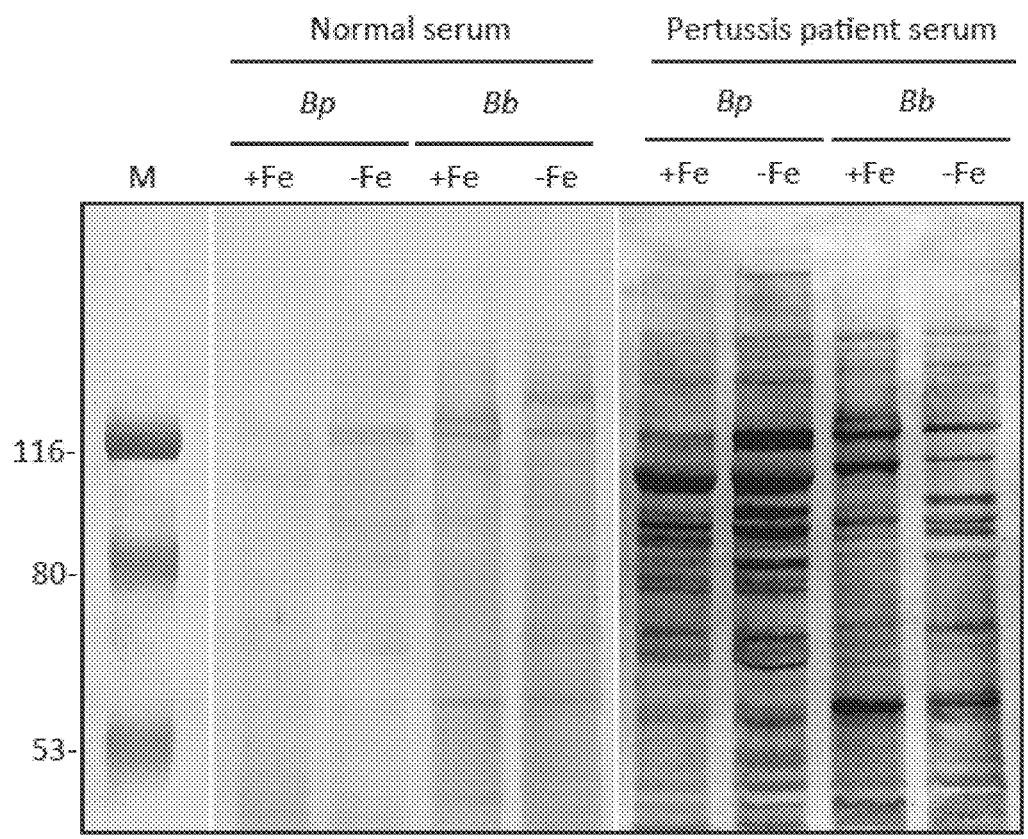
Figure 1B:
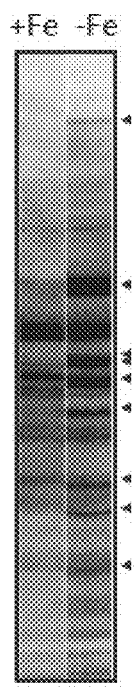
Figure 1C:
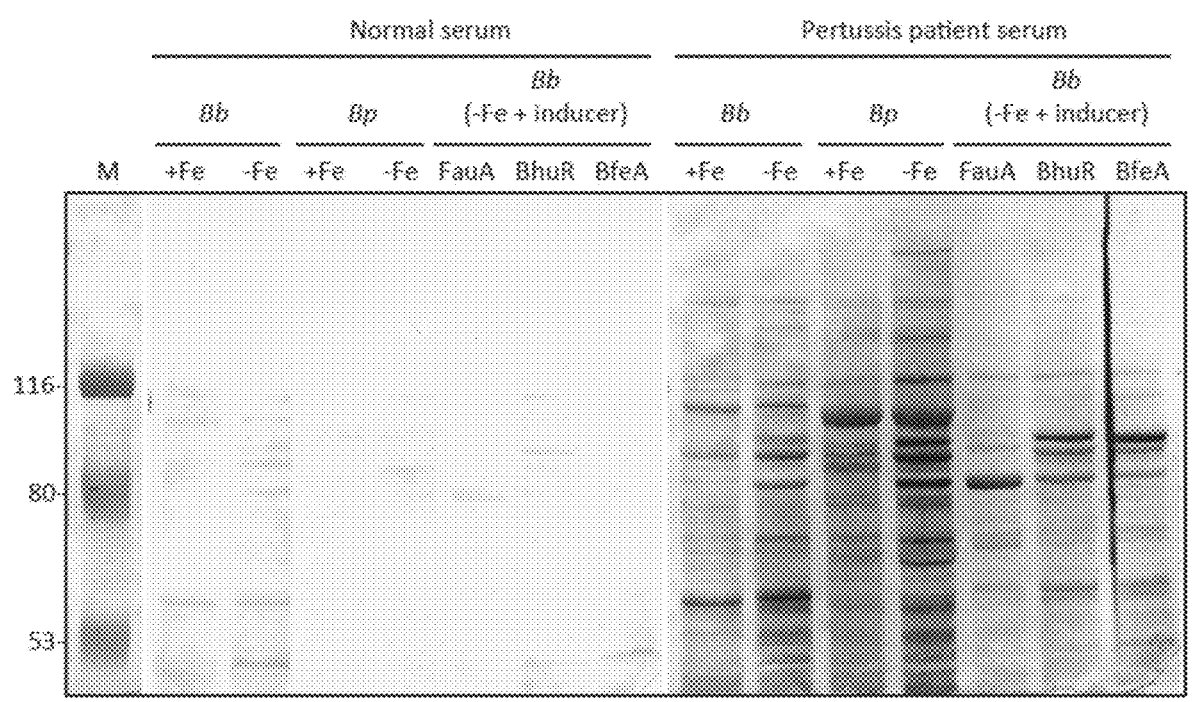

US010799573B2

(12) United States Patent
Brickman et al.

(10) Patent No.: US 10,799,573 B2
(45) Date of Patent: Oct. 13, 2020

(54) PERTUSSIS VACCINES AND METHODS OF MAKING AND USING

(71) Applicant: Regents of the University of Minnesota, Minneapolis, MN (US)

(72) Inventors: Timothy Joseph Brickman, Roseville, MN (US); Sandra Kay Armstrong, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/474,594

(22) Filed: Mar. 30, 2017

(65) Prior Publication Data

US 2017/0333547 A1 Nov. 23, 2017

Related U.S. Application Data

(60) Provisional application No. 62/315,356, filed on Mar. 30, 2016.

(51) Int. Cl.

| | |
|---|---|
| *A61K 39/10* | (2006.01) |
| *A61K 39/00* | (2006.01) |
| *A61K 39/02* | (2006.01) |
| *C07K 14/235* | (2006.01) |
| *C12N 1/20* | (2006.01) |

(52) U.S. Cl.
CPC .......... *A61K 39/099* (2013.01); *C07K 14/235* (2013.01); *C12N 1/20* (2013.01); *A61K 2039/52* (2013.01); *A61K 2039/521* (2013.01); *A61K 2039/70* (2013.01); *C07K 2319/32* (2013.01)

(58) Field of Classification Search
CPC ...... A61K 39/099; A61K 38/00; A61K 39/00; C07K 2319/00
See application file for complete search history.

(56) References Cited

U.S. PATENT DOCUMENTS

| | | | | |
|---|---|---|---|---|
| 2003/0039660 A1* | 2/2003 | King | C07K 14/43568 | 424/185.1 |
| 2007/0116711 A1* | 5/2007 | Castado | A61K 39/099 | 424/190.1 |
| 2009/0081725 A1* | 3/2009 | Powell | A61K 39/0208 | 435/69.1 |
| 2012/0207776 A1* | 8/2012 | Serino | C07K 14/245 | 424/190.1 |
| 2017/0340725 A1* | 11/2017 | Ciaramella | A61K 39/12 | |

OTHER PUBLICATIONS

Brickman et al., ASM2015 Society for Microbiology; Jan. 15, 2015 (Year: 2015).*
Brickman and Armstrong, "Essential role of the iron-regulated outer membrane receptor FauA in alcaligin siderophore-mediated iron uptake in *Bordetella* species," *J Bacteriol.*, 181(19):5958-5966, Oct. 1999.
Brickman et al., "Bordetella iron transport and virulence," *Biometals.*, 20(3-4):303-322, Jun. 2007.
Brickman et al., "Differential expression of bordetella pertussis iron transport system genes during infection," *Mol Microbiol.*, 70(1):3-14, Oct. 2008.
Brickman et al "Heme transport contributes to in vivo fitness of Bordetella pertussis during primary infection in mice," *Infect Immun.*, 74(3):1741-1744, Mar. 2006.
Brickman et al., "Production of bordetella pertussis iron receptor proteins and fimbrial protein-iron receptor chimeras for evaluation as vaccine antigens," *ASM2015 115th General Meeting: American Society for Microbiology.*, Jan. 15, 2015, Abstract Only.

Brickmanet al., "Impact of alcaligin siderophore utilization on in vivo growth of Bordetella pertussis," *Infect Immun.*, 75(11):5305-5312, Nov. 2007.

Brumbaugh et al., "Immunization with the yersiniabactin receptor, FyuA, protects against pyelonephritis in a murine model of urinary tract infection," *Infect Immun.*, 81(9):3309-3316, Sep. 2013.

Cherry, JD., "Pertussis: challenges today and for the future," *PLoS Pathogens.*, 9(7):e1003418, Jul. 25, 2013.

Clark et al., "Pertussis control: time for something new?" *Trends Microbiol.*, 20(5):211-213, May 2012.

GenBank Accession No. BP0996, "Bordetella pertussis Tohama I chromosome, complete genome," Dec. 17, 2014, 2 pages.

GenBank Accession No. BP1119, "Bordetella pertussis Tohama I chromosome, complete genome," Dec. 17, 2014, 2 pages.

GenBank Accession No. BP1568, "Bordetella pertussis Tohama I chromosome, complete genome," Dec. 17, 2014, 2 pages.

GenBank Accession No. BP2674, "Bordetella pertussis Tohama I chromosome, complete genome," Dec. 17, 2014, 2 pages.

Mattoo and Cherry., "Molecular pathogenesis, epidemiology, and clinical manifestations of respiratory infections due to *Bordetella pertussis* and other *Bordetella* subspecies ," *Clin Micro Rev.*, 18(2):326-382, Apr. 2005.

Melvin et al., "Bordetella pertussis pathogenesis: current and future challenges," *Nat Rev Microbiol.*, 12(4):274-288, Apr. 2014.

Mobberley-Schuman et al., "Phagocytosis of Bordetella pertussis incubated with convalescent serum," *J Infect Dis.*, 187(10):1646-1653, May 15, 2003.

Sheldon et al., "Iron acquisition strategies of bacterial pathogens," *Microbiol Spectr.*, 4(2), Apr. 2016.

(Continued)

*Primary Examiner* — Gary B Nickol
*Assistant Examiner* — Lakia J Jackson-Tongue
(74) *Attorney, Agent, or Firm* — Fish & Richardson P.C.

(57) ABSTRACT

*Bordetella pertussis* iron receptor proteins or portions thereof (e.g., one or more extracellular domains), alone or spliced into *B. pertussis* scaffold proteins (e.g., fimbrial or flagellin), are provided and can be used in acellular vaccines to protect against pertussis or other *Bordetella* diseases in humans and non-human mammals. In addition, *Bordetella* species grown under iron-starved conditions are provided and can be used in whole cell vaccines to protect against pertussis or other *Bordetella* diseases in humans and non-human mammals.

12 Claims, 18 Drawing Sheets

Specification includes a Sequence Listing.

(56) References Cited

OTHER PUBLICATIONS

Vanderpool and Armstrong., "The Bordetella bhu locus is required for heme iron utilization," *J Bacteriol.*, 183(14):4278-4287, 2001.

Warfel and Edwards., "Pertussis vaccines and the challenge of inducing durable immunity," *Curr Opin Immunol.*, 35:48-54, Aug. 2015.

Weinberg, Ed., "Iron availability and infection," *Biochim Biophys Acta.*, 1790(7):600-605, Jul. 2009.

Williamson and Matthews., "Epitope mapping the Fim2 and Fim3 proteins of Bordetella pertussis with sera from patients infected with or vaccinated against whooping cough," *FEMS Immunol Med Microbiol*, 13(2):169-178, Feb. 1996.

Witt et al., "Unexpectedly limited durability of immunity following acellular pertussis vaccination in preadolescents in a North American outbreak," *Clin Infect Dis.*, 54(12):1730-1735, Jun. 15, 2012.

\* cited by examiner

PERTUSSIS VACCINES AND METHODS OF MAKING AND USING

CROSS REFERENCE TO RELATED APPLICATIONS

This application claims the benefit of priority under 35 U.S.C. 119(e) to U.S. Application No. 62/315,356 filed Mar. 30, 2016.

FEDERALLY SPONSORED RESEARCH OR DEVELOPMENT

This invention was made with government support under AI031088 awarded by the National Institutes of Health. The government has certain rights in the invention.

TECHNICAL FIELD

This disclosure generally relates to vaccines.

BACKGROUND

Bordetella pertussis is the bacterial agent of whooping cough (pertussis). The primary pertussis vaccines currently in use in the U.S. are acellular (e.g., INFANRIX and BOOSTRIX (GlaxoSmithKline); DAPTACEL and ADACEL (Sanofi Pasteur) [infant and adult formulations for each, respectively]). The pertussis component of these vaccines contains detoxified pertussis toxin and two surface proteins (e.g., filamentous hemagglutinin, pertactin), while DAPTACEL and ADACEL also contain fimbrial (Fim) proteins, Fim2 and Fim3. For a number of different reasons (e.g., current acellular pertussis vaccines do not provide durable immunity; current acellular pertussis vaccines prevent disease symptoms but do not prevent B. pertussis colonization; and/or B. pertussis strains have been isolated from patients that lack a particular protein component of the vaccine), these acellular vaccines have been ineffective in preventing colonization and transmission of B. pertussis. Therefore, a new approach to impart immunity against B. pertussis is needed.

SUMMARY

Currently used acellular pertussis vaccines typically include a small set of antigens representing three or four virulence factors from B. pertussis. It is now apparent from the significant increase in *pertussis* cases and from epidemiological studies that these acellular vaccines lack the desired level of efficacy and duration of protection.

This disclosure provides a solution to this problem by describing polypeptides that can be used as vaccines to inoculate against one or more *Bordetella* species (e.g., *B. pertussis, B. parapertussis, B. bronchiseptica*, and/or *B. avium*). The vaccines described herein provide significantly improved immunity against *B. pertussis* over existing acellular pertussis vaccines. Further, a similar strategy can be applied to provide a whole-cell pertussis vaccine that imparts improved immunity relative to the whole-cell pertussis vaccines that are used in many countries throughout the world.

In one aspect, a chimeric polypeptide is provided that includes at least one antigenic polypeptide and a scaffold protein.

In some embodiments, the at least one antigenic polypeptide includes an iron receptor protein or an antigenic portion thereof. In some embodiments, the antigenic portion of an iron receptor protein includes at least one extracellular domain. In some embodiments, the iron receptor protein is a TonB-dependent receptor protein or an antigenic portion thereof. A representative TonB-dependent receptor protein is a ferric enterobactin siderophore (BfeA) receptor protein. In some embodiments, the iron receptor protein is a hemin or hemoprotein receptor or an antigenic portion thereof. A representative hemin or hemoprotein receptor is a BhuR protein. In some embodiments, the iron receptor protein is a siderophore receptor or an antigenic portion thereof. A representative siderophore receptor is an alcaligin siderophore receptor (FauA).

In some embodiments, the scaffold protein is a fimbrial protein or a flagellin protein. Representative fimbrial proteins include, without limitation, a fimbrial 2 protein or fimbrial 3 protein. A representative flagellin protein is a flagellin subunit protein.

In one aspect, a nucleic acid molecule encoding a polypeptide as described herein (e.g., a chimeric polypeptide) is provided. In another aspect, a construct that includes such a nucleic acid molecule is provided. In still another aspect, a host cell that includes such a nucleic acid molecule or construct is provided.

In another aspect, an acellular *B. pertussis* vaccine for protecting a subject against infection by *B. pertussis, B. parapertussis, B. bronchiseptica* and/or *B. avium* is provided. Such a vaccine typically includes a chimeric polypeptide as described herein and a pharmaceutically acceptable carrier. In some embodiments, such an acellular vaccine further includes an adjuvant.

In still another aspect, a whole cell *B. pertussis* vaccine for protecting a subject against infection by *B. pertussis, B. parapertussis, B. bronchiseptica* and/or *B. avium* is provided. Such a vaccine typically includes a composition of *B. pertussis* grown under iron-starvation conditions and a pharmaceutically acceptable carrier. In some embodiments, such a whole cell vaccine further includes an adjuvant.

In yet another aspect, a method of vaccinating a subject against *B. pertussis* is provided. Such a method typically includes administering a polypeptide as described herein (e.g., a chimeric polypeptide) or a vaccine as described herein to a subject. Representative subjects include, without limitation, humans, canines, pigs, rabbits, cats, or birds.

In still another aspect, a method of making an acellular *B. pertussis* vaccine is provided. Such a method typically includes providing a polypeptide as described herein (e.g., a chimeric polypeptide); or expressing a nucleic acid molecule or construct as described herein; or culturing a host cell as described herein (e.g., a host cell expressing a nucleic acid molecule or construct as described herein); and combining the polypeptide produced therefrom with a pharmaceutically acceptable carrier. In some embodiments, such a method further includes adding an adjuvant.

In yet another aspect, a method of making a whole-cell *B. pertussis* vaccine is provided. Such a method typically includes culturing *B. pertussis* under iron-starvation conditions; and processing the *B. pertussis* grown under iron-starvation conditions into a whole-cell vaccine. In some embodiments, such a method further includes adding an adjuvant.

In one aspect, a polypeptide that includes at least one extracellular domain of an iron receptor protein is provided. In some embodiments, the iron receptor protein is a heme, hemin or hemoprotein receptor (e.g., a BhuR protein). In some embodiments, the iron receptor protein is a siderophore receptor (e.g., an alcaligin siderophore receptor

[FauA]). In some embodiments, the iron receptor protein is a TonB-dependent receptor protein (e.g., an enterobactin siderophore receptor protein [BfeA]).

In another aspect, a chimeric polypeptide that includes a scaffold protein or portion thereof and at least one antigenic polypeptide is provided. In some embodiments, the at least one antigenic polypeptide is spliced into a scaffold protein. Representative scaffold proteins include a fimbrial 2 or a fimbrial 3 protein or a flagellin protein. In some embodiments, the at least one antigenic polypeptide includes at least one extracellular domain of an iron receptor protein. In some embodiments, the at least one antigenic polypeptide includes an iron receptor protein. In some embodiments, the at least one antigenic polypeptide includes at least one extracellular domain of a TonB-dependent receptor protein. In some embodiments, the at least one antigenic polypeptide includes a TonB-dependent receptor protein.

In still another aspect, a nucleic acid molecule is provided that encodes any of the polypeptides described herein. In yet another aspect, a construct is provided that includes a nucleic acid molecule as described herein. In another aspect, a host cell is provided that includes a nucleic acid molecule as described herein or a construct as described herein.

Figure 6:
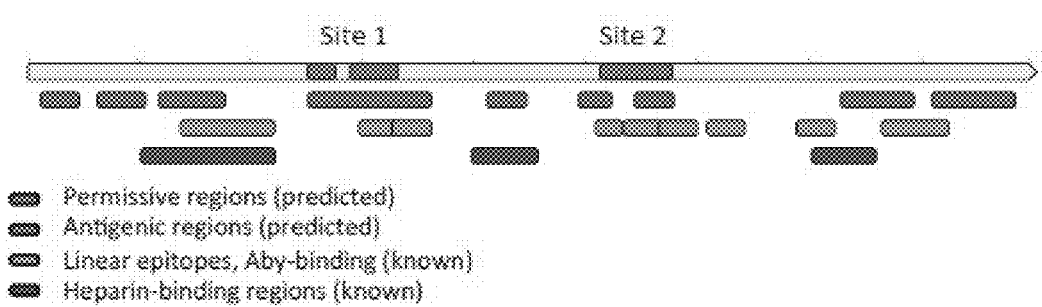

In one aspect, an acellular *B. pertussis* vaccine is provided for protecting a subject against infection by *B. pertussis, B. parapertussis, B. bronchiseptica* and/or *B. avium*. Such a vaccine typically includes any of the polypeptides described herein. In another aspect, a whole cell *B. pertussis* vaccine is provided for protecting a subject against infection by *B. pertussis, B. parapertussis, B. bronchiseptica* and/or *B. avium*. Such a vaccine typically includes *B. pertussis* grown under iron-starved conditions that promote the production of iron receptors. In some embodiments, a vaccine further can include an adjuvant.

In still another aspect, a method of vaccinating a subject against *B. pertussis* is provided. Such a method typically includes administering, to a subject, any of the polypeptides described herein, any of the nucleic acid molecules described herein, any of the constructs described herein, any of the host cells described herein, or any of the vaccines described herein. In some embodiments, the subject is a human, a canine, a pig, a rabbit, a cat, or a bird.

In still another aspect, a method of making an acellular *B. pertussis* vaccine is provided. Such a method typically includes providing any of the polypeptides described herein; or expressing any of the nucleic acid molecules described herein; or expressing any of the constructs described herein; or culturing any of the host cells described herein; and combining the polypeptide produced therefrom with a pharmaceutically acceptable carrier. In yet another aspect, a method of making a whole-cell *B. pertussis* vaccine is provided. Such a method typically includes culturing *B. pertussis* under iron-starvation conditions that enhance iron receptor production; and processing the iron-starved *B. pertussis* cells for delivery as a vaccine. In some embodiments, such a method further includes adding an adjuvant.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1A is a photograph of an immunoblot showing total membranes proteins prepared from *B. pertussis* (Bp) and *B. bronchiseptica* (Bb) cultured under iron-replete (+Fe) and iron-depleted (−Fe) conditions probed using human sera from normal uninfected donors and from infected *pertussis* patients.

FIG. 1B is a photograph showing the juxtaposition of *B. pertussis* FIG. 1A *pertussis* patient immunoblot lanes; immunoreactive iron-regulated proteins are indicated with small triangles.

FIG. 1C is a photograph showing total membrane proteins of *B. pertussis* and *B. bronchiseptica*, and outer membrane proteins from *B. bronchiseptica* strains that overproduce the FauA, BhuR or BfeA receptors of *B. pertussis*, probed using sera from normal and culture-positive donors (different donors than in FIG. 1A).

FIG. 2 is a graph showing that *B. pertussis* mutants lacking the FauA and BhuR receptors are attenuated in competition infections using a mouse model of pertussis. Mice (5/group) were co-infected with a 1:1 mixture of wild type *B. pertussis* and a receptor mutant derivative. Bacterial colony forming units (CFU) of each strain pair in the lungs and trachea were determined at different times post-infection. The competitive index is the ratio of the mutant/wild-type CFU ratio recovered at each time point divided by the mutant/wild-type CFU ratio in the input inoculum (mean values shown). A competitive index of <1 indicates the mutant strain is less fit (exhibits less growth in mice) compared with the wild type parent strain. A plot (grey line) showing CFU levels typical of *B. pertussis* mouse respiratory tract infections is overlaid for reference. A *B. pertussis* fauA mutant is defective for growth in the mouse throughout infection and a bhuR mutant is most defective during late infection. A double mutant lacking both fauA and bhuR is avirulent.

FIG. 3 is a schematic showing the structural domains of the *B. pertussis* FauA and BhuR receptor proteins, including the cell surface-exposed loops that connect the antiparallel transmembrane beta strands (wide yellow ribbons). Both proteins have 11 flexible extracellular loops (within dashed boxes in structures, and dark regions within "Barrel" region). BhuR has an additional N-terminal extension (NTE) involved in cell surface signaling. A linear depiction of the loop domain locations is shown below the structures.

FIG. 4A shows a photograph of a SDS-PAGE gel showing purification of polyHis-tagged Bp FauA protein produced in *Escherichia coli*. M, molecular mass markers; Total, total cell proteins; 1-4, eluate fractions from immobilized metal affinity chromatography.

FIG. 4B shows a photograph of an immunoblot using rabbit antiserum raised to recombinant FauA to probe outer membrane proteins of iron-starved *B. pertussis* strains. WT, wild-type *B. pertussis*; ΔfauA, *B. pertussis* fauA in-frame deletion mutant; ΔfauA/fauA+, *B. pertussis* ΔfauA mutant complemented using the wild type fauA gene carried on a plasmid.

FIG. 5A is a schematic showing an expression system for production of Fim3 and Fim3-iron receptor chimeras in *B. pertussis*.

FIG. 5B is a schematic showing gene assembly using a thermostable ligase cycling reaction.

FIG. 6 is a schematic showing a map of *B. pertussis* Fim3 functional domains. Regions predicted to be permissive for foreign epitope insertion are shown in red.

Figure 7A:
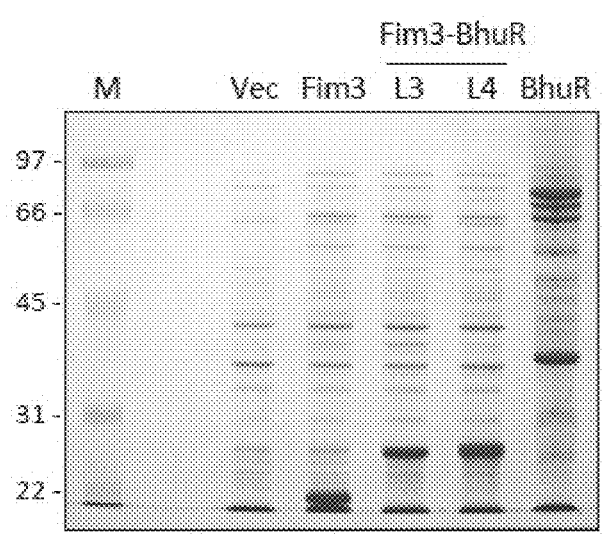
Figure 7B:
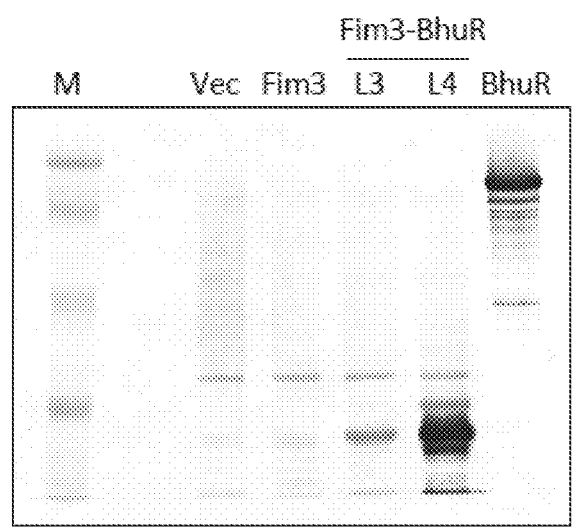
Figure 8A:
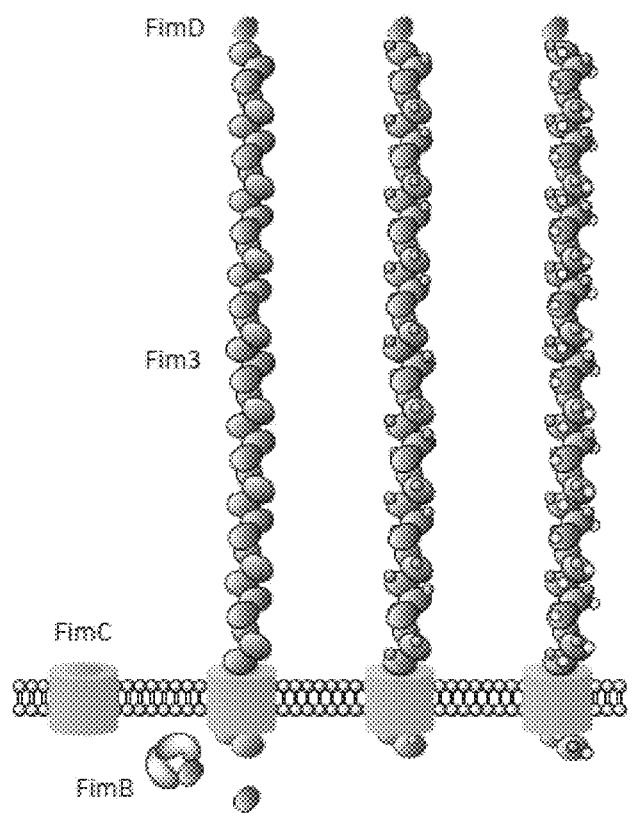
Figure 8B:
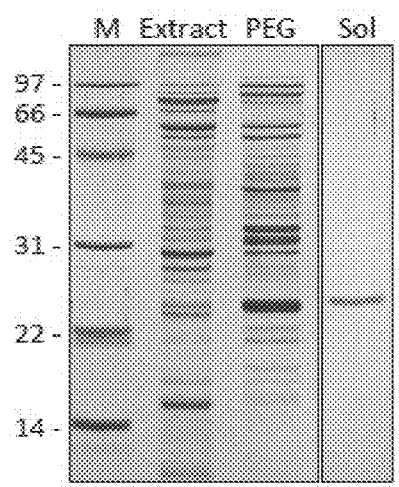
Figure 9A:
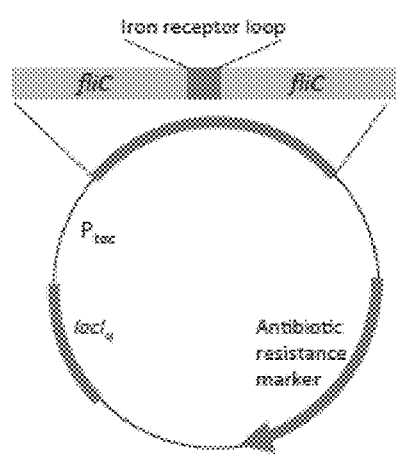
Figure 9B:
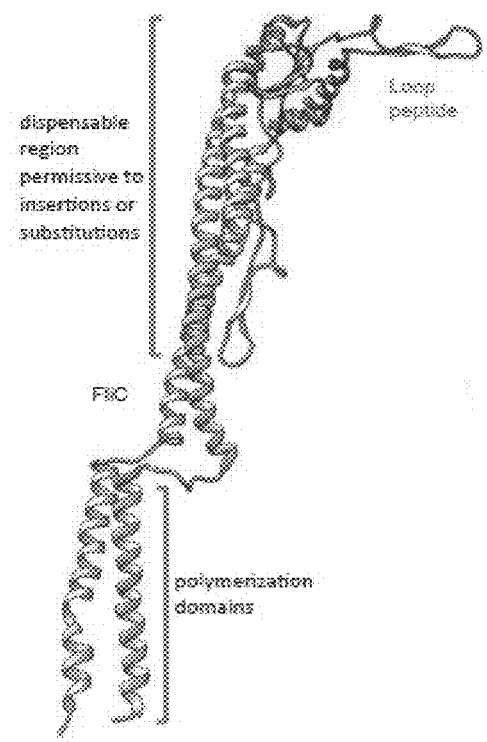
Figure 9C:
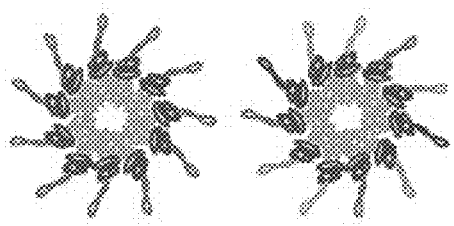
Figure 9D:
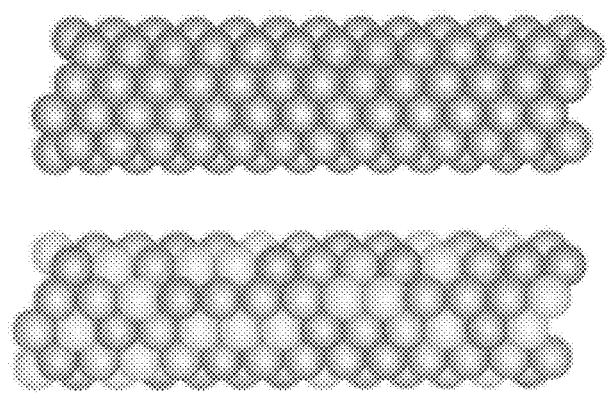

FIG. 7A is a photograph of a SDS-PAGE gel showing Fim3 and two Fim3-BhuR loop domain chimeric proteins produced in *E. coli*. M, molecular mass markers; Vec, vector control; Fim3, Fim3 of *B. pertussis*; L3, Fim3 with BhuR loop 3; L4, Fim3 with BhuR loop 4; BhuR, outer membrane proteins of BhuR-over-producing *B. pertussis* cells.

FIG. 7B is a photograph of an immunoblot of a duplicate gel (as shown in FIG. 7A) probed with BhuR-specific rabbit antiserum, demonstrating reactivity with the Fim3-BhuR loop 3 and Fim3-BhuR loop 4 chimeric proteins.

FIG. 8A is a schematic showing a model of multivalent Fim3-iron receptor chimeric protein filaments on the *B. pertussis* cell surface. Grey ovals, Fim3 fimbrial subunits; red and yellow spheres, iron receptor loop domains displayed on the fimbrial scaffold.

FIG. 8B is a photograph of a SDS-PAGE gel showing extraction and purification of overproduced *B. pertussis* Fim3 protein filaments. M, molecular mass markers; Extract, urea extract of *B. pertussis* cells; PEG, Fim3 precipitated from urea extract using PEG 600; Sol, Fim3 filaments after solubilization of PEG 600 precipitate (Fim3, ca. 20 kDal).

FIG. 9A is a map of a plasmid for production of flagellin-iron receptor chimeric proteins in *E. coli*, with inducible expression driven from the tac promoter under LacI repressor control. The site for in-frame insertion of iron receptor loop encoding DNA segments within fliC is shown.

FIG. 9B is a model of a flagellin-iron receptor chimeric protein monomer, showing the dispensible region of FliC that is permissive to peptide insertions or substitutions, and the polymerization domains involved in self-assembly of the flagellar filament. The loop peptide is shown in red.

FIG. 9C shows a top view of proposed hybrid flagellar filaments having 11 subunits per turn and with exposed iron receptor loops (filaments displaying a single or multiple different iron receptor loops are shown).

FIG. 9D is a side view of proposed hybrid flagellar filaments shown in FIG. 9C.

DETAILED DESCRIPTION

The mammalian host is a very iron-poor environment; in order to multiply and cause disease, bacterial pathogens must use their iron uptake systems to overcome host iron restriction. Such iron uptake systems include bacterial cell surface proteins (e.g., receptors) that help take up iron-containing heme from the host or iron-loaded bacterial siderophores. Such proteins, however, have not been previously used as *pertussis* vaccine antigens. The immune response to vaccination using these receptor proteins (or antigenic domains thereof) would target essential bacterial processes by blocking iron uptake, thus preventing the establishment of infection, and also by promoting clearance of the organism. By targeting iron uptake systems that *Bordetella* or other genera of bacteria requires at both early and later stages of infection, more effective bacterial clearance and protection can be achieved.

This strategy can be used to produce acellular *pertussis* vaccines. Acellular vaccines typically are preferred in the U.S. Therefore, polypeptides are provided herein that include at least one domain (e.g., an extracellular domain) from a protein that is induced in response to low iron availability or iron starvation. These proteins typically are receptors that transport iron-bound molecules (e.g., siderophores or heme) or iron-carrying proteins, or just the iron, into the cell. These proteins are referred to herein as "iron receptor proteins." Such iron receptor proteins, or portions thereof, can be used as antigens in vaccine compositions.

There are a number of different iron receptor proteins that can be used in an acellular pertussis vaccine as described herein. Simply by way of example, an iron receptor protein can be a receptor for a heme protein, or a receptor for a siderophore, or a receptor for another iron source or nutrient that is also a TonB-dependent receptor. A heme receptor includes, without limitation, a BhuR protein (e.g., gene locus tag BP0347); a siderophore receptor includes, without limitation, an alcaligin siderophore receptor (FauA; e.g., gene locus tag BP2463) or an enterobactin siderophore receptor (BfeA; e.g., gene locus tag BP2901), or a catechol or catecholamine receptor (e.g., BfrA, BfrD, BfrE); and a TonB-dependent receptor includes, without limitation, TonB-dependent receptors for iron as well as TonB-dependent receptors for one or more nutrients or co-factor (see, for example, Table 1).

TABLE 1

*Bordetella* TonB-dependent outer membrane receptors

| Characterized receptors of known substrate specificity | | |
|---|---|---|
| Receptor name | Locus Tag[a] | Iron Source Substrate |
| FauA | BP2463, BPP3450, BB3900 | alcaligin |
| BfeA | BP2901, BPP2495, BB1942 | enterobactin |
| BhuR | BP0347, BPP4185, BB4655 | heme |
| BfrA | BB4761 | catecholamine, catechol |
| BfrD | BP0856, BPP3376, BB3826 | catecholamine, catechol |
| BfrE | BP0857, BPP3375, BB3825 | catecholamine, catechol |

| Predicted receptors of unknown substrate specificity | |
|---|---|
| Receptor name | Locus Tag[a] |
| BfrB | BP2016, BPP2396, BB1846 |
| BfrC | BP3663, BPP0079, BB0078 |
| BfrF | BP0736, BPP3688, BB4122 |
| BfrG | BP2922, BPP1078, BB1294 |
| BfrH | BP1138, BPP3206, BB3658 |
| BfrI | BP1962, BPP2334, BB1785 |
| BfrZ | BB4744 |
| HemC | BP0456, BPP4370, BB4956 |
| — | BPP2457, BB1905 |
| — | BP3101, BPP0746, BB0832 |
| — | BP3595, BPP3984, BB4457 |
| — | BP3077, BPP0186, BB0189 |
| — | BP1760, BPP1991, BB2179 |

[a]BP, *B. pertussis*; BPP, *B. parapertussis*; BB, *B. bronchiseptica*

TonB-dependent receptors are bacterial outer membrane proteins that bind and transport ferric iron chelates (siderophores), heme, vitamin $B_{12}$, as well as other substrates. High affinity transport of TonB-dependent receptor substrates across the outer membrane requires a proton-motive force, with the energy transduced by the TonB-ExbB-ExbD inner membrane protein complex. The structures of twelve TonB-dependent receptors have been solved (some alone, some with bound ligands, and some complexed with TonB), and forty-five crystal structures now exist for comparison. All known TonB-dependent receptors have the same domain architecture, and it is likely that all TonB-dependent receptors have this general structure—they all have a twenty-two-stranded transmembrane beta-barrel surrounding a globular plug domain, and a TonB-interacting domain. The twenty-two beta-strands that traverse back and forth across the outer membrane to form the beta-barrel are joined on the extracellular and periplasmic aspects by loop segments. The extracellular loop segments, along with residues on the extracellular side of the plug domain, form the specific ligand binding sites. These extracellular loops are surface-exposed, solvent-accessible, and highly flexible, and are specific for binding their cognate substrate. The strong conservation of TonB-dependent receptor domain architecture allows for accurate prediction of the transmembrane beta-strands and the extracellular loop domains using freely available protein modeling algorithms such as PRED-TMBB, I-TASSER, ROBETTA, and SPARKS-X starting with known TonB-dependent receptor structural data as templates.

Figure 2:
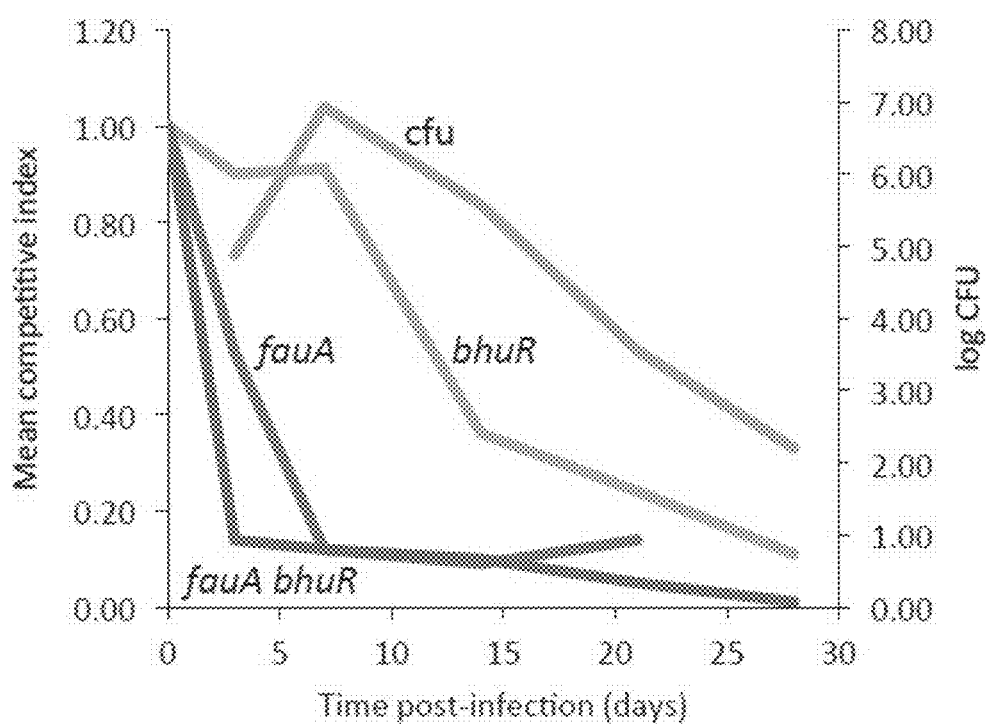
Figure 3:
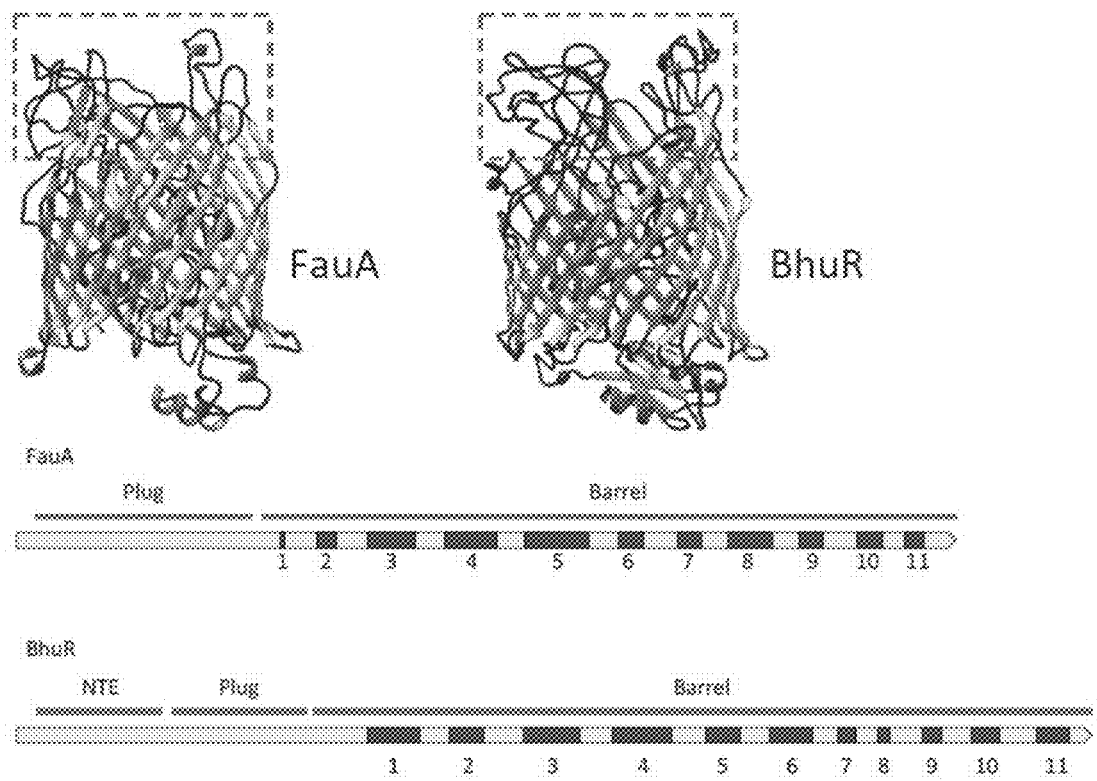
Figure 4A:
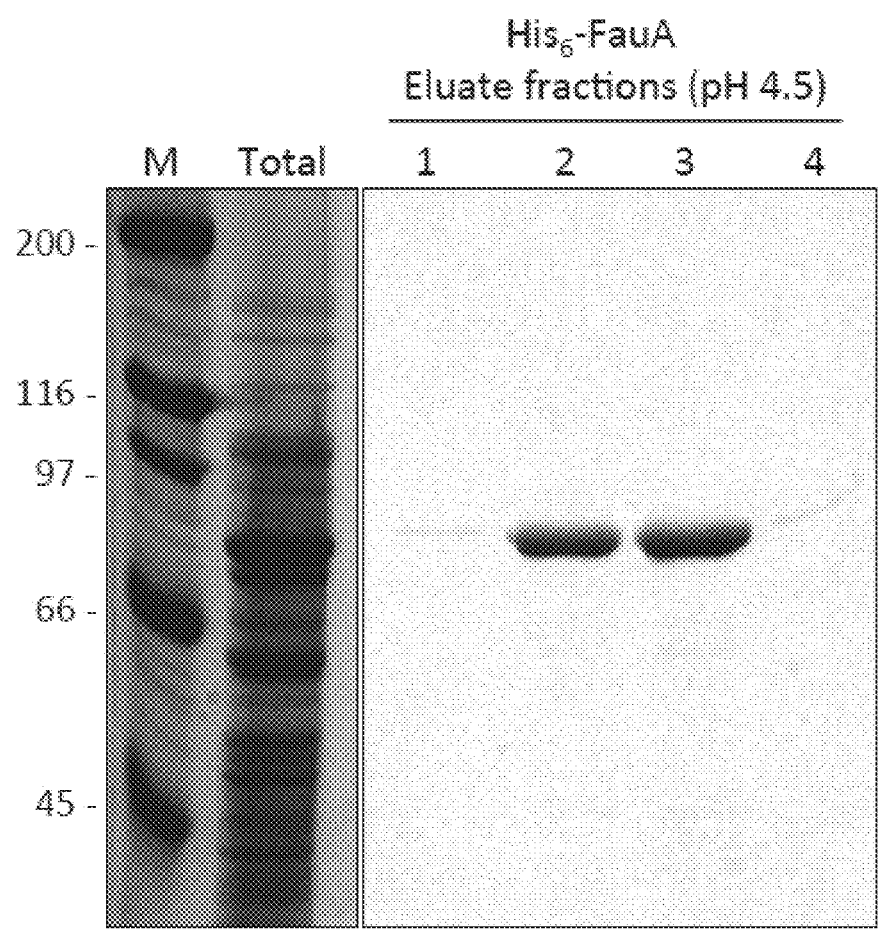
Figure 4B:
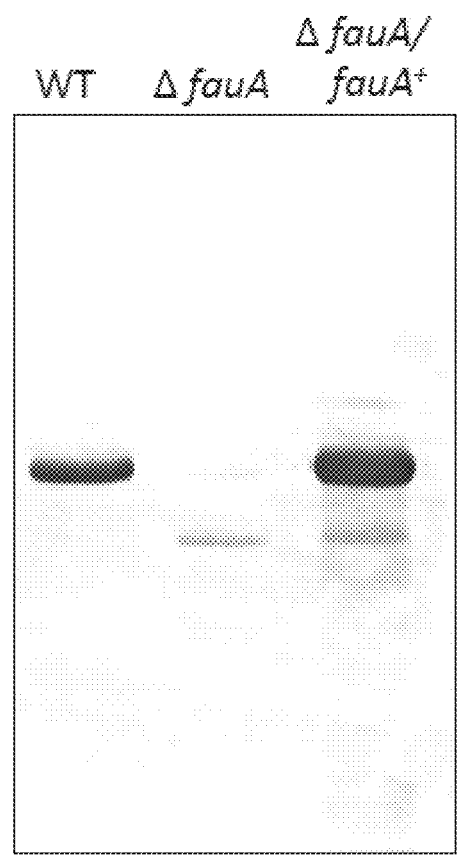
Figure 5A:
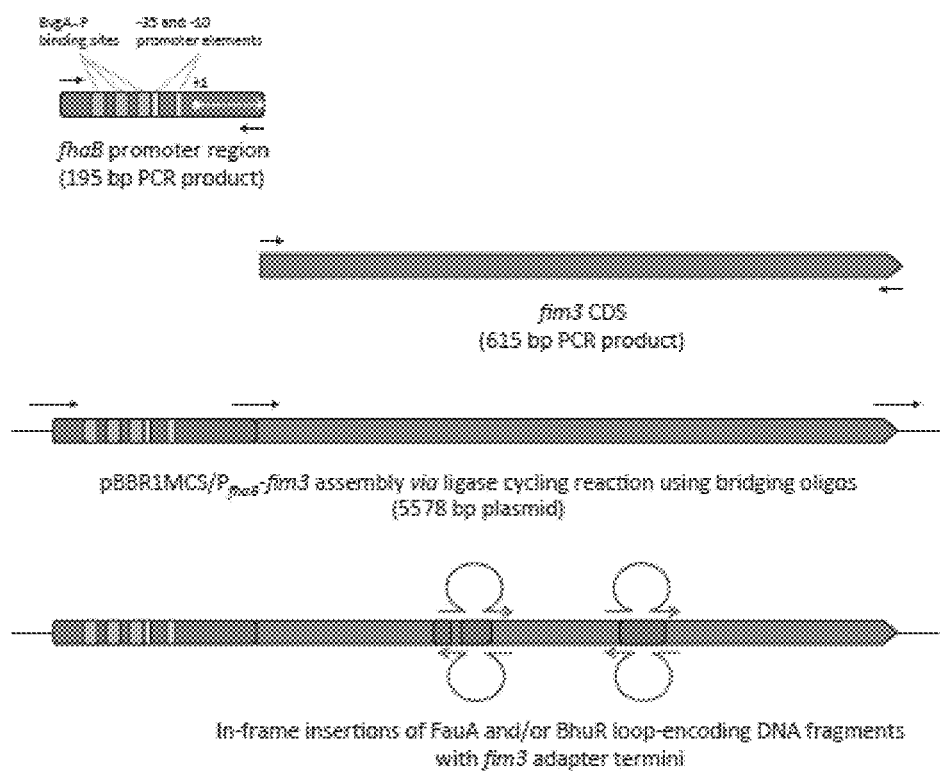
Figure 5B:
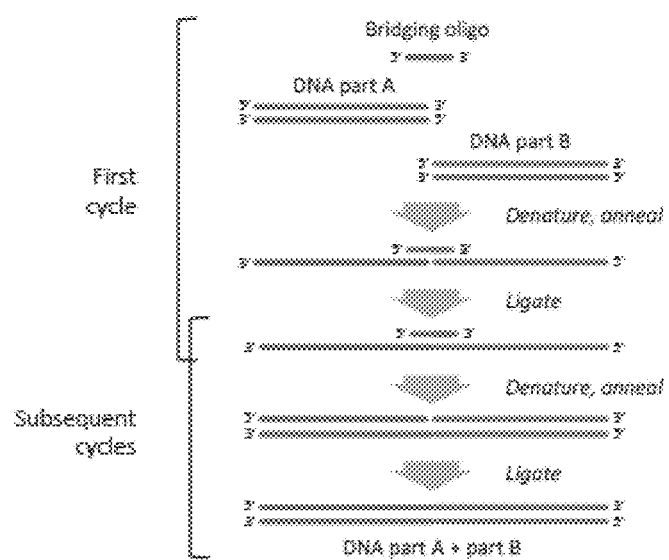

Experimental results (see, for example, FIG. 2) show that FauA is needed for *B. pertussis* growth throughout the course of mouse infection, and BhuR is required for growth during late infection, when host heme sources become available due to tissue damage. Thus, elimination of both FauA and BhuR renders *B. pertussis* avirulent Targeting by vaccines of nutrient receptors that are important during different stages of infection provides broader protection against the bacteria not only attempting to colonize, but also against those already colonizing and persisting in the respiratory tract.

One or more of the iron receptor proteins, or portions thereof, described herein for use as antigens in vaccine compositions can be displayed within one or more scaffold proteins. Scaffold proteins provide the benefit of increased antigen multivalency, which imparts enhanced immunogenicity. Multivalent antigens more effectively crosslink adjacent B-cell receptors (antigen-specific surface immunoglobulins) to initiate the signaling cascade that induces B-cell proliferation and differentiation. Furthermore, the extended cross-linking confers high avidity on the antigen-B-cell interaction. Multivalent antigens displaying a particular receptor loop domain on a polymeric fimbrial or flagellar scaffold can be used singly as vaccine antigens, or they can be dissociated into monomeric subunits, mixed, and reassorted to produced multivalent antigens displaying multiple different receptor loop domains. These polyvalent antigens can be used to generate immune responses to multiple distinct receptor loop domains.

A scaffold protein can be one or more fimbrial (Fim) or flagellin proteins into which specific regions or domains of an antigenic polypeptide are introduced. *B. pertussis* Fim2 and Fim3 proteins are already currently used in some existing acellular vaccine formulations. For example, an antigenic polypeptide or portions thereof (e.g., a first antigenic polypeptide or portions thereof, a second antigenic polypeptide or portions thereof, optionally, a third antigenic polypeptide or portions thereof, a fourth antigenic polypeptide or portions thereof, etc., etc.) can be spliced into regions of the fimbrial protein such that the fimbrial protein acts as a scaffold to display the antigenic polypeptide(s). Representative fimbrial proteins include, without limitation, fimbrial protein X ("FimX"), fimbrial protein 2 ("Fim2") or fimbrial protein 3 ("Fim3"). Without limitation, the sequences of various fim genes and Fim proteins can be found, e.g., in GenBank Accession Nos. BP1568, BP1119, BP2674, and their orthologs in other *Bordetella* species.

Flagellin proteins are the major subunits of bacterial flagella, and have been used to produce vaccine antigens for many viral and bacterial agents. Flagellin proteins have broadly conserved structural features, and large insertions that replace the variable solvent-exposed region of *E. coli* flagellin are remarkably well tolerated without affecting flagellar export, assembly, or function. In addition to providing high antigen valence, flagellin polymers are recognized by the innate immune system as a pathogen-associated molecular pattern molecule, stimulating adaptive immunity. Representative flagellin proteins include, e.g., FliC and FlaA, and, without limitation, the sequences of various flagellin genes and flagellin proteins can be found, e.g., in GenBank Accession Nos. BP0996 and its orthologs in other *Bordetella* species, and b1923 and its orthologs in *E. coli* and *Salmonella* spp.

One way to accomplish this is to express one or more antigenic proteins, or portions thereof, and a scaffold protein in one or more chimeric polypeptides. Such chimeric polypeptides can be genetically constructed using recombinant methods known in the art. Such chimeric polypeptides result in polymeric, multivalent antigens that are highly effective vaccines. As discussed herein, an antigenic polypeptide or a portion thereof can be one or more of the iron receptor proteins described herein or a portion thereof (e.g., one or more of the TonB-dependent receptor proteins described herein, or a portion thereof).

Polypeptides are provided herein that can be used as vaccines against *B. pertussis* or other *Bordetella* species. As indicated herein, a polypeptide used in a vaccine can be an iron receptor protein or a chimeric polypeptide that includes at least one scaffold protein into which an antigenic polypeptide has been inserted (e.g., an iron receptor protein and/or another antigenic polypeptide). As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

In addition, nucleic acids encoding such polypeptides are provided herein. As used herein, nucleic acids can include DNA and RNA, and includes nucleic acids that contain one or more nucleotide analogs or backbone modifications. A nucleic acid can be single stranded or double stranded, which usually depends upon its intended use. As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Similarly, nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Also provided are nucleic acids and polypeptides that differ in sequence from the wild type sequence. Nucleic acids and polypeptides that differ in sequence from the corresponding wild type sequence can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to the corresponding wild type sequence. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). See, e.g., Chenna et al., 2003, Nucleic Acids Res., 31(13):3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

A construct, also referred to as a vector, containing a nucleic acid (e.g., a nucleic acid that encodes a polypeptide as described herein for use in a vaccine) is provided. Constructs, including expression constructs, are commercially available or can be produced by recombinant DNA techniques routine in the art. A construct containing a nucleic acid can have expression elements, and further can include sequences such as those encoding a selectable marker (e.g., an antibiotic resistance gene). A construct containing a nucleic acid can be fused to a second polypeptide that, for example, can be used in purification of the encoded polypeptide (e.g., a 6× tag polypeptide, a glutathione S-transferase (GST) polypeptide)

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid. Expression elements in a construct can be operably linked to a coding sequence in cis or in trans; expression elements that are operably linked to a coding sequence in trans may be in-frame with the coding sequence.

Constructs as described herein can be introduced into a host cell. As used herein, "host cell" refers to the particular cell into which a construct is introduced and also includes the progeny of such a cell that carry the construct. A host cell can be any prokaryotic or eukaryotic cell. For example, nucleic acids can be expressed in bacterial cells such as *E. coli*, or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

A similar strategy that takes advantage of the *pertussis* bacterial requirement for iron can be used to produce whole-cell *pertussis* (wP) vaccines. Whole-cell vaccines typically are preferred in many non-U.S. countries around the world. Similar to the strategy described above for acellular vaccines, *B. pertussis* grown under iron-starvation conditions can be used in a whole-cell vaccine. Since the whole-cell *pertussis* vaccines currently being used are produced by growing bacterial cells in iron-rich medium, the bacteria in those vaccines will not have produced their iron receptors and will lack those important antigens. On the other hand, iron-starved *B. pertussis* produces abundant amounts of iron uptake receptors. For example, alcaligin siderophore production is evidence of iron starvation in *B. pertussis*. Alcaligin siderophore production level can be assessed using a siderophore detection assay such as a chrome azurol S universal siderophore assay, or using growth stimulation assays of siderophore-deficient mutant *Bordetella* indicator strains. Iron receptor protein production levels in iron-starved *B. pertussis* cells can be assessed by sodium dodecyl sulfate polyacrylamide gel electrophoresis (SDS-PAGE) analysis of bacterial cell proteins, and/or by immunoblot analysis using iron receptor specific antisera. As with the acellular vaccines, an immune response against the iron uptake receptors targets essential bacterial processes by blocking iron uptake, preventing a productive infection and promoting immune clearance.

Any of the polypeptides described herein (e.g., an iron receptor protein or a chimeric polypeptide including a scaffold protein and an antigenic polypeptide) can be used in an acellular vaccine to protect a subject against infection by *B. pertussis*. Similarly, the iron-starved *B. pertussis* described herein can be used in a whole-cell vaccine to protect a subject against infection by *B. pertussis*.

Vaccines are well-known in the art, and often include a pharmaceutically acceptable carrier. As used herein, "pharmaceutically acceptable carrier" is intended to include any and all excipients, solvents, dispersion media, coatings, antibacterial and anti-fungal agents, isotonic and absorption delaying agents, and the like, compatible with administration. Pharmaceutically acceptable carriers for delivering compounds are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12$^{th}$ Ed., 2001, McGraw-Hill Co. The type of pharmaceutically acceptable carrier used in a particular formulation can depend on various factors, such as, for example, the physical and chemical properties of the compound, the route of administration, and the manufacturing procedure. Vaccines often include an adjuvant, in addition to the primary antigen, to further increase the immune response by the subject.

The vaccines described herein (e.g., an acellular vaccine including an iron receptor protein or a chimeric polypeptide including a scaffold protein and an antigenic polypeptide or a whole-cell vaccine including iron-starved *B. pertussis* cells) can be used in a method of vaccinating or immunizing a subject against a *B. pertussis* infection (e.g., a productive infection). Additionally or alternatively, vaccinating or immunizing a subject can prophylactically protect the subject against infection by *B. pertussis*.

The vaccines described herein can be administered in an effective amount to a subject. Typically, an effective amount is an amount that prevents or treats a *Bordetella* infection in a subject without inducing any adverse effects. The amount of polypeptide in each dose of vaccine typically is the minimal amount that induces an immunoprotective response in a subject without significant, adverse side effects. The particular amount of polypeptide in a vaccine will vary depending upon the antigenicity of the polypeptide as well as the presence of any adjuvant. In some instances, a vaccine dose includes between about 1 µg and about 1000 µg of protein (e.g., about 1 µg to about 200 µg; about 1 µg to about 50 µg; or about 1 µg to about 10 µg of protein) in a volume of about 50 µl to about 2 ml per dose (e.g., about 100 µl to about 1.5 ml; about 250 µl to about 1 ml; about 100 µl to about 500 µl; or about 100 µl to about 250 µl). A whole cell vaccine dose is standardized to Opacity Units using a WHO reference preparation (IU), with one vaccine dose not exceeding 20 IU.

The vaccines described herein can be administered to any subject that can be infected with a *Bordetella* species. For example, *B. pertussis* and *B. parapertussis* infect humans, while *B. bronchiseptica* occasionally infects humans but also infects other mammals such as canines and felines (causing kennel cough) and pigs (causing atrophic rhinitis) and *B. avium* infects birds (causing turkey rhinotracheitis). Alternatively, the strategy described herein can be used to make an acellular or whole-cell vaccine from another *Bordetella* species. A vaccine as described herein typically is formulated to be compatible with its intended route of administration. Suitable routes of administration include, without limitation, intranasal, oral, topical, pulmonary, ocular, intestinal, and parenteral administration. Routes for parenteral administration include intravenous, intramuscular, and subcutaneous administration, as well as intraperitoneal, intra-arterial, intra-articular, intracardiac, intracisternal, intradermal, intralesional, intraocular, intrapleural, intrathecal, intrauterine, and intraventricular administration. For example, a vaccine as described herein can be delivered subcutaneously.

The vaccines described herein can be made using methods that are known in the art. For example, the acellular vaccines described herein can be made by combining any of the polypeptides described herein (e.g., an iron receptor protein or a chimeric polypeptide including a scaffold protein and an antigenic polypeptide) with a suitable pharmaceutically acceptable carrier. A polypeptide for use in a *pertussis* vaccine as described herein can be purified, or a polypeptide for use in a *pertussis* vaccine as described herein can be expressed from an appropriate nucleic acid (e.g., contained within a construct; contained within a host cell).

In addition, the whole-cellular vaccines described herein can be made by combining iron-starved *B. pertussis* cells (e.g., *B. pertussis* cells cultured under reduced iron or iron-starvation conditions) with a pharmaceutically acceptable carrier. Iron starvation can be achieved by sub-culturing *B. pertussis* from iron-replete culture media to culture media lacking iron supplementation, or by the addition of non-utilizable iron chelators to iron-replete culture medium. As discussed herein, the production of alcaligin siderophore or other iron receptor proteins are evidence of iron starvation in *B. pertussis*, and methods of evaluating the production levels of alcaligin siderophore or other iron receptor proteins in iron-starved *B. pertussis* cells are described herein and are known in the art. It would be appreciated that the cell culture may need to be processed in one or more ways prior to being combined with the pharmaceutically acceptable carrier. For example, the cells in the cell culture can be collected and washed to remove the iron-depleted media. Additionally or alternatively, iron-starved cells can be, for example, frozen or lyophilized.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1

Production of Whole Cell Pertussis (wP) Vaccines

*B. pertussis* frozen stocks (in whole sheep blood, stored at −80° C.) were streaked onto Bordet Gengou agar plates and cultured at 37° C. for 48 h. Plate growth was suspended in complete Stainer-Scholte liquid medium, and used to inoculate seed cultures in complete Stainer-Scholte medium. After 36 to 48 h growth at 37° C. in a shaking incubator, bacteria were harvested by centrifugation, and the bacterial cells were washed at least twice using iron-free Stainer-Scholte medium. This washed seed suspension was used to inoculate complete Stainer Scholte medium (+Fe) or iron-free Stainer Scholte medium (−Fe) to an initial cell density corresponding to ~2×10$^8$ cfu/ml (~0.1 OD$_{600}$), and grown for 36 to 48 h at 37° C. in a shaking incubator. Iron starvation status in iron-free cultures was confirmed by a siderophore detection assay. *B. pertussis* cells were harvested by centrifugation, and washed 3 times using cold sterile saline solution.

Bacteria were suspended in saline to an optical density representing ~1×10$^9$ cfu/ml (confirmed by plate counts), killed by heating at 65° C. for 0.5 h and adsorbed to alum (Alhydrogel®, 2%, InvivoGen) to yield +Fe and −Fe wP vaccine suspensions.

Example 2

Production of Recombinant B. pertussis Iron Receptor Proteins in E. coli

B. pertussis iron receptor genes were PCR-amplified from genomic DNA templates, and cloned into pBAD/His plasmid vectors (Invitrogen) for arabinose-inducible expression in *E. coli*. PCR primers were designed to include restriction site adapters for cloning, and to replace the receptors' start codons and N-terminal signal sequences with the plasmid vector-encoded start codon and polyhistidine tag for affinity purification of the products.

*E. coli* strain TOP10 (F-mcrA Δ(mrr-hsdRAIS-mcrBC) φ80lacZΔM15 ΔlacX74 mpG recA1 araD139 Δ(ara-leu) 7697 galE15 galK16 rpsL(Str$^R$) endA1λ$^-$) (Invitrogen) carrying recombinant pBAD/His plasmids was cultured overnight on Luria-Bertani agar plates supplemented with ampicillin (200 μg/ml), then sub-cultured into Luria-Bertani broth supplemented with ampicillin and grown at 37° C. in a shaking incubator until mid-exponential phase. Arabinose (20% w/v solution) was added to 0.002% final concentration to induce receptor gene expression, and the cultures were grown for an additional 4 h. Bacterial cells were recovered by centrifugation, washed using 1/10 culture volume STE (50 mM Tris pH 8, 100 mM NaCl, 1 mM EDTA), and resuspended in 1/10 culture volume STE before freezing the suspension overnight at −80° C.

Thawed cell suspensions were disrupted using a French pressure cell, and the insoluble cell fraction was recovered by ultracentrifugation. The insoluble material was washed using 1/10 culture volume of TE (10 mM Tris, 1 mM EDTA pH 8.0), followed by washing using 1/10 culture volume of water.

The insoluble material was then suspended in 1/10 culture volume of DB (100 mM $NaH_2PO_4$, 10 mM Tris, 8 M urea) at a pH 8.0, and any insoluble material was removed by centrifugation and discarded.

The supernatant fluid containing solubilized receptor proteins was transferred to a 50-ml conical tube containing $Ni^{2+}$-charged Chelating Sepharose Fast-Flow beads (Amersham) equilibrated in DB (pH 8.0), and bound on a rotating platform for 1 h at room temperature. The beads were pelleted gently, and the supernatant fluid containing the unbound proteins was discarded. The beads were gently resuspended in DB (pH 6.3) to wash away loosely-bound proteins, then the beads were again pelleted gently and the supernatant fluid was discarded. After repeating the wash with DB (pH 6.3), the slurry was transferred to a disposable column fitted with a glass fiber support. The column bed was eluted 4 times, each time using ½ bed volume of DB (pH 5.9), and the eluates were collected separately. Elution was repeated, except using DB (pH 4.5), and, again, the eluates were collected separately. Eluate fractions were analyzed by SDS-PAGE for the presence of the receptor proteins. Peak fractions were pooled and the receptor proteins were precipitated by the addition of an equal volume of acetone at −20° C. After 30 min at −20° C., the protein precipitate was recovered by centrifugation, briefly air-dried, then dissolved in TE containing 8 M urea. After removing any insoluble material by centrifugation, the cleared protein solution was rapidly diluted into 10 volumes of 10 mM CHAPS in TE to renature the protein. The protein solution was cleared by centrifugation or using a centrifugal filter unit with a 0.22 μm filter. Soluble receptor protein concentration was determined using the Bradford assay.

Example 3

Construction of Recombinant Plasmids Encoding *B. pertussis* Fimbriae-Iron Receptor Protein Chimeras The fim3 coding sequences with stop codon, and the fhaB promoter region were each PCR amplified using *B. pertussis* genomic DNA template and 5'-phosphorylated oligonucleotide primers. The resulting products were combined with SmaI-linearized plasmid vector pBBR1MCS-5 by the ligase cycling reaction using bridging oligonucleotides to yield recombinant plasmid pBB5/P (fhaB-fim3). This plasmid places fim3 expression under the control of the strong, well-characterized Bvg-dependent fhaB filamentous hemagglutinin promoter, thus circumventing the negative influence of the fim3 downstream repressive element on fim3 expression, and the polyC tract involved in fim3 phase variation. The plasmid construct was verified by nucleotide sequencing, and SDS-PAGE analysis confirmed that *B. pertussis* carrying plasmid pBB5/PfhaB-fim3 overproduces the Fim3 protein. Sub-regions of *B. pertussis* iron receptor genes encoding known or predicted extracellular loop domains of the receptor proteins were PCR-amplified using oligonucleotide primers with fim3 adapters. The products were recombined with fim3 by PCR megaprimer cloning atfim3 sites predicted to be permissive for foreign peptide insertion without interference with fimbrial assembly and maturation in *B. pertussis*. Plasmids encoding Fim3-iron receptor chimeric proteins were confirmed by nucleotide sequencing, then transferred to *B. pertussis* by mating.

TABLE 2

FauA extracellular loop domains

| Extra cellular loop | Amino acids | FauA amino acid residues | SEQ ID NO |
|---|---|---|---|
| 1 | 205-209 | GSWDY | 1 |
| 2 | 235-250 | SQGDSYVHFLDTRRRT | 2 |
| 3 | 274-312 | NHSNGFGSGFPLFYSDGSRTDFNRSVANNAPWARQDTEA | 3 |
| 4 | 336-375 | TDGRYLMKHVYRGGYPDRHTGIIAAPPAFSNYDGNLDRDD | 4 |
| 5 | 398-448 | MSIDNHSDIQRYAMVGPAPAIGSFFDWRRAHIQEPSWADTLSPADDVRTKQ | 5 |

TABLE 2-continued

FauA extracellular loop domains

| Extra cellular loop | Amino acids | FauA amino acid residues | SEQ ID NO |
|---|---|---|---|
| 6 | 472-492 | SDWKTKQMYFGSRREYRIKNQ | 6 |
| 7 | 518-537 | QPQNARDTSGGILPPIKSKS | 7 |
| 8 | 558-593 | FQTRQDNLAQVIPGSSIPGFPNMQASRAASGAKVEG | 8 |
| 9 | 615-633 | FTTKDASGNPINTNHPRSL | 9 |
| 10 | 658-679 | QSRMYQAAASPRGNVEVEQDSY | 10 |
| 11 | 701-711 | NNLFDKKYYDQ | 11 |

TABLE 3

BhuR extracellular loop domains

| Extra cellular loop | Amino acids | BhuR amino acid residues | SEQ ID NO: |
|---|---|---|---|
| 1 | 274-316 | HDDTSWLLQAGTRNGHDLDNRADTGGYGSKRSQPSPEDYAQNN | 12 |
| 2 | 338-367 | FKRRADLDQMYQQGAGTSYQYGANRTHEET | 13 |
| 3 | 397-442 | QRLRLDSSQDARRTRDGRAYARPGDPYFYGYPSGPYGRSNSIQESI | 14 |
| 4 | 468-515 | YGNRTEQYSDGYDNCPAIPPGTPAPMGPRLCDMLHTNQADMPRVKGSQ | 15 |
| 5 | 542-569 | YEQKPQQGGGYQNNPNAGALPPSSSGGR | 16 |
| 6 | 595-627 | RAPSATELYTNYGGPGTYLRVGNPSLKPETSKG | 17 |
| 7 | 648-660 | NRYQNFIDKNVPL | 18 |
| 8 | 680-690 | TGLANRARVRI | 19 |
| 9 | 714-730 | AVGKDENTGQHLNSVPP | 20 |
| 10 | 755-778 | RRDDVQYPEASASARYADFQAPGY | 21 |
| 11 | 806-836 | DKKYWEAINVPTAGAIAIPRPLDWYNEPGRS | 22 |

TABLE 4

PCR primers for production of DNA segments for ligase cycling assembly for construction of fim3-expressing plasmid pBB5/PfhaB-fim3

| Target region | Forward primer | SEQ ID NO | Reverse primer | SEQ ID NO: | Product size (bp) |
|---|---|---|---|---|---|
| fhaB promoter | TACGTGCCGGACAGGGTTT | 23 | ATTCCGACCAGCGAAGTGAAG | 24 | 195 |
| fim3 CDS | ATGTCCAAGTTTTCATACCCTGC | 25 | TCAGGGGTAGACGACGGAAA | 26 | 615 |

TABLE 5

Bridging oligonucleotides for ligase cycling assembly with SmaI-cut plasmid vector pBBR1MCS-5 for construction of pBB5/PfhaB-fim3

| Vector | Sequence | SEQ ID NO: |
|---|---|---|
| pBBR1MCS-5 vector/fhaB promoter | GCTCTAGAACTAGTGGATCCCCCTACGTGCCGGACAGGGTTT | 27 |
| fhaB promoter/ fim3 CDS | CTTCACTTCGCTGGTCGGAATATGTCCAAGTTTTCATACCCTGC | 28 |
| fim3/ pBBR1MCS-5 vector | TTTCCGTCGTCTACCCCTGAGGGCTGCAGGAATTCGATATCA | 29 |

TABLE 6

Fim3 regions predicted to be permissive for iron receptor loop domain insertion

| Predicted Fim3 permissive site | Fim amino acid residues | SEQ ID NO: | Amino acid residues | Nucle TABLE 9-continued B. pertussis Tohama I fim3 DNA sequence (SEQ ID NO: 41):

GCGTGGAGTTCCGCCTGGCCAACCTCAACGGCCAGCACATCCGCATGGGC
ACGGACAAAACCACGCAAGCCGCGCAAACCTTTACCGGCAAGGTCACCAA
TGGCAGCAAGAGCTACACCCTGCGCTATCTCGCCTCGTACGTGAAGAAAC
CCAAGGAAGATGTCGACGCGGCCCAGATCACCAGCTACGTCGGCTTTTCC
GTCGTCTACCCCTGA

TABLE 10

B. pertussis Tohama I Fim3 amino acid sequence (SEQ ID NO:42):

MSKFSYPALRAALILAASPVLPALANDGTIVITGSISDQTCVIEEPSTLN
HIKVVQLPKISKNALRNDGDTAGATPFDIKLKECPQALGALKLYFEPGIT
TNYDTGDLIAYKQTYNASGNGNLSTVSSATKAKGVEFRLANLNGQHIRMG
TDKTTQAAQTFTGKVTNGSKSYTLRYLASYVKKPKEDVDAAQITSYVGFS
VVYP

TABLE 11

Extracellular loop domains of three other Bordetella TonB-dependent receptor proteins

| HemC | Extra cellular loop | Amino acids | Amino acid residues | SEQ ID NO |
|---|---|---|---|---|
| | 1 | 100-122 | DTEDVKIVLDGAPKGFEKYRQGS | 43 |
| | 2 | 156-231 | DTKDAADLLPPGARFGALAKYGRHSNDGQDIYSVAL YGRTRADGADGLLYANRRDGGDLRRPDGTRFAYSRNNQRS | 44 |
| | 3 | 253-290 | SNAAGWQPFAAKRDDLPAPSQADIDRYGLTEAWRRKLV | 45 |
| | 4 | 320-418 | ARSDTRQRDRRSSRASQSAFLGTLGNKSWVDYRDDR FDLSNESHVALGTAEHVLLAGLRWHRHRRDTLMYYP PGRGEPDYNHGYFQPHYMPSGTQTVRS | 46 |
| | 5 | 441-458 | VANTGRPNDAPRYNNPAP | 47 |
| | 6 | 481-485 | KAARG | 48 |
| | 7 | 510-526 | AKSNVSGSSRALRPERI | 49 |
| | 8 | 554-595 | FRNRGKHEIFQRRGVACRGQAEGGAASDCPKPLSNYRNLPGY | 50 |
| | 9 | 624-643 | RDASPRDPWGPRTWIAEIPP | 51 |
| | 10 | 668-693 | VRRQDRSPTDGDPLAGYWALPKTAGY | 52 |
| | 11 | 717-738 | DNLFNRPYHPYLGEAVSGTGRN | 53 |
| BfeA | Extra cellular loop | Amino acids | Amino acid residues | |
| | 1 | 191-203 | YTNQPEDSREGNT | 54 |
| | 2 | 227-259 | NKTNPDARDINAGHANTSDNGNPSTAGREGVIN | 55 |
| | 3 | 285-317 | QGNLFAGDTMNNANSDFSDSLYGKETNAMYREN | 56 |
| | 4 | 340-369 | TRNARQREGLAGGPEGAPTAGGYDTARLKN | 57 |
| | 5 | 395-430 | LRESLEDPAGTRQTYTGGAIGGTAPADRDPKSRQTS | 58 |
| | 6 | 456-462 | NSEFGSN | 59 |
| | 7 | 488-529 | KAPNLYQSNPNYLLYSRGNGCLASQTNTNGCYLVGNEDLSPE | 60 |
| | 8 | 552-589 | FRNDYRNKIVAGTDVQYRLANGARVLQWTNSGKAVVEG | 61 |
| | 9 | 615-628 | KEKATGEPLSVIPE | 62 |
| | 10 | 652-675 | YGKQEGPSTNVRTGVELNGDGRQT | 63 |
| | 11 | 705-728 | DKQLYREGNASSAGAATYNEPGRA | 64 |
| BP3077 | Extra cellular loop | Amino acids | Amino acid residues | |
| | 1 | ... | ... | |
| | 2 | 227-251 | LKRRSSDYRVPDWPDGKLAGSYSES | 65 |

TABLE 11-continued

Extracellular loop domains of three other Bordetella TonB-dependent receptor proteins

| | | | |
|---|---|---|---|
| 3 | 274-339 | LESKYGLPGHNHEYEGCHPHGSHLHCGGHDDHGHGH DEHEEGEAEHDHGHEHGAGDVPYVKLRSNR | 66 |
| 4 | 363-383 | TDYRHDEIEGGQLGTRFQNRG | 67 |
| 5 | 409-427 | SDFRATGEEAFLPRSKTRA | 68 |
| 6 | 452-467 | QRVSPQSGAPASRTAG | 69 |
| 7 | 493-524 | RLPSAQELYADGVHLATNTYEIGDPGLDRETS | 70 |
| 8 | 547-576 | NRVKNYIYANTLDRYEDFRLIEYTQRDAEF | 71 |
| 9 | 600-616 | VRGRLTGGGGNLPRIPA | 72 |
| 10 | 639-657 | VYRQDDIAAYESSTPGYDM | 73 |
| 11 | 680-704 | NNLLNKLAFNHASFISTVAPLPGRS | 74 |

Example 4

Purification of Fim3-Iron Receptor Chimeric Proteins Produced in *B. pertussis*

Fimbriae were extracted from *B. pertussis* cells recovered from Stainer-Scholte liquid cultures by incubation in a solution of 4 M urea in phosphate-buffered saline at 60° C. for 30 min with gentle agitation, followed by precipitation with 4% PEG 600. In addition, the fim3-iron receptor encoding insert DNA fragments of pBB5/PfhaB-fim3 derivatives were sub-cloned into plasmid vector pET-3a for inducible T7 promoter-directed expression and high-level production of chimeric proteins in *E. coli.*

Example 5

Construction of Recombinant Plasmids Encoding *B. pertussis* Iron Receptor-Flagellin Protein Chimeras Polyvalent iron receptor antigens are produced using the FliC protein as a display scaffold. Individual *B. pertussis* receptor loop domain coding sequences are spliced in-frame into the dispensable region of fliC borne on a ColE1 plasmid (a pBR322 derivative). Construction of FliC-loop domain chimeras use PCR-generated loop-encoding DNA segments as megaprimers. Expression is driven from the tac promoter under LacI control, and the product is exported and assembled on the bacterial surface as flagella. Flagella (5-10% total cell protein) are easily purified after mechanical shearing from the bacterium and dissociation into monomers at reduced pH. Purified FliC monomers readily polymerize into filaments (ca. 20,000-30,000 monomers) in physiological pH solution by seeding with small flagellar fragments. Different FliC-receptor loop fusion protein monomers are produced in *E. coli* and purified from its flagella, then combined and assembled in vitro to produce polyvalent vaccine antigen polymers displaying multiple different iron receptor loop domains.

Example 6

Results

FIG. 1 are exemplary photographs showing that serum from culture-positive human donors ("*pertussis* patient serum") reacts with *Bordetella* iron source receptors. Sera were from *B. pertussis* culture-positive children (aged 6 to 17 years old, previously vaccinated, n=12) and a control group of normal adult donors not known to have been infected with *B. pertussis* (n=10).

FIG. 2 shows results of mouse infection studies that evidence the importance of alcaligin siderophore and heme iron utilization systems to in vivo fitness of *B. pertussis* at different stages of infection. FIG. 2 shows that a mutant *B. pertussis* strain lacking the FauA and BhuR receptors was severely attenuated in the mouse *pertussis* model.

FIG. 4 are photographs showing the production of the polyhistidine-tagged iron receptor proteins in *E. coli* and purification by metal affinity chromatography. FauA is shown simply as an example. Note that the FauA-specific antiserum shows negligible cross-reactivity with other iron receptor proteins. Similar results were obtained for the BhuR heme receptor protein, demonstrating that the receptor proteins are immunogenic.

The plasmid construct shown in FIG. 5A directs expression of Fim3 from the strong Bvg-dependent fhaB promoter, thus eliminating the influence of the downstream repressive element in the Fim3 initial transcribed region and the Fim3 promoter poly(C)-tract effecting phase-variant expression. *B. pertussis* expresses the accessory genes necessary for fimbrial assembly and export.

In addition, two different BhuR receptor protein extracellular loop domains were each spliced into site 1 within the Fim3 fimbrial protein (FIG. 6) and the chimeric products were overproduced in *E. coli*. FIG. 7 shows that the FIG. 3-loop chimeric proteins (L3, L4) were strongly reactive with rabbit antisera raised to the purified recombinant BhuR receptor protein. This result indicates that immunization using a chimeric protein as described herein may elicit an anti-iron receptor immune response in a subject that can block colonization and/or enhance immune recognition and clearance of the *B. pertussis.*

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A chimeric polypeptide comprising at least one *Bordetella* antigenic polypeptide comprising an iron receptor protein or an antigenic portion thereof spliced into a *Bordetella* scaffold protein selected from a fimbrial protein, a flagellin protein, and combinations thereof.

2. The chimeric polypeptide of claim 1, wherein the antigenic portion of an iron receptor protein comprises at least one extracellular domain.

3. The chimeric polypeptide of claim 1, wherein the iron receptor protein is a TonB-dependent receptor protein or an antigenic portion thereof.

4. The chimeric polypeptide of claim 3, wherein the TonB-dependent receptor protein is a ferric enterobactin siderophore (BfeA) receptor protein.

5. The chimeric polypeptide of claim 1, wherein the iron receptor protein is a hemin or hemoprotein receptor or an antigenic portion thereof.

6. The chimeric polypeptide of claim 5, wherein the hemin or hemoprotein receptor is a BhuR protein.

7. The chimeric polypeptide of claim 1, wherein the iron receptor protein is a siderophore receptor or an antigenic portion thereof.

8. The chimeric polypeptide of claim 7, wherein the siderophore receptor is an alcaligin siderophore receptor (FauA).

9. The chimeric polypeptide of claim 1, wherein the fimbrial protein is a fimbrial 2 protein or fimbrial 3 protein.

10. The chimeric polypeptide of claim 1, wherein the flagellin protein is a flagellin subunit protein.

11. An acellular immunogenic composition, comprising the chimeric polypeptide of claim 1 and a pharmaceutically acceptable carrier.

12. The acellular vaccine of claim 11, further comprising an adjuvant.

* * * * *

UNITED STATES PATENT AND TRADEMARK OFFICE
CERTIFICATE OF CORRECTION

PATENT NO. : 10,799,573 B2
APPLICATION NO. : 15/474594
DATED : October 13, 2020
INVENTOR(S) : Brickman et al.

Page 1 of 1

It is certified that error appears in the above-identified patent and that said Letters Patent is hereby corrected as shown below:

In the Claims

Column 52, Line 16, Claim 12, delete "vaccine" and insert -- immunogenic composition --.

Signed and Sealed this
Twenty-second Day of March, 2022

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 74

<210> SEQ ID NO 1
<211> LENGTH: 5
<212> TYPE: PRT
<213> ORGANISM: Bordetella pertussis

<400> SEQUENCE: 1

Gly Ser Trp Asp Tyr
1               5

<210> SEQ ID NO 2
<211> LENGTH: 16
<212> TYPE: PRT
<213> ORGANISM: Bordetella pertussis

<400> SEQUENCE: 2

Ser Gln Gly Asp Ser Tyr Val His Phe Leu Asp Thr Arg Arg Arg Thr
1               5                   10                  15

<210> SEQ ID NO 3
<211> LENGTH: 39
<212> TYPE: PRT
<213> ORGANISM: Bordetella pertussis

<400> SEQUENCE: 3

Asn His Ser Asn Gly Phe Gly Ser Gly Phe Pro Leu Phe Tyr Ser Asp
1               5                   10                  15

Gly Ser Arg Thr Asp Phe Asn Arg Ser Val Ala Asn Asn Ala Pro Trp
            20                  25                  30

Ala Arg Gln Asp Thr Glu Ala
        35

<210> SEQ ID NO 4
<211> LENGTH: 40
<212> TYPE: PRT
<213> ORGANISM: Bordetella pertussis

<400> SEQUENCE: 4

Thr Asp Gly Arg Tyr Leu Met Lys His Val Tyr Arg Gly Tyr Pro
1               5                   10                  15

Asp Arg His Thr Gly Ile Ile Ala Ala Pro Pro Ala Phe Ser Asn Tyr
            20                  25                  30

Asp Gly Asn Leu Asp Arg Asp Asp
        35                  40

<210> SEQ ID NO 5
<211> LENGTH: 51
<212> TYPE: PRT
<213> ORGANISM: Bordetella pertussis

<400> SEQUENCE: 5

Met Ser Ile Asp Asn His Ser Asp Ile Gln Arg Tyr Ala Met Val Gly
1               5                   10                  15
```

```
Pro Ala Pro Ala Ile Gly Ser Phe Phe Asp Trp Arg Ala His Ile
                20                  25                  30

Gln Glu Pro Ser Trp Ala Asp Thr Leu Ser Pro Ala Asp Val Arg
        35                  40                  45

Thr Lys Gln
    50

<210> SEQ ID NO 6
<211> LENGTH: 21
<212> TYPE: PRT
<213> ORGANISM: Bordetella pertussis

<400> SEQUENCE: 6

Ser Asp Trp Lys Thr Lys Gln Met Tyr Phe Gly Ser Arg Arg Glu Tyr
1               5                   10                  15

Arg Ile Lys Asn Gln
            20

<210> SEQ ID NO 7
<211> LENGTH: 20
<212> TYPE: PRT
<213> ORGANISM: Bordetella pertussis

<400> SEQUENCE: 7

Gln Pro Gln Asn Ala Arg Asp Thr Ser Gly Ile Leu Pro Pro Ile
1               5                   10                  15

Lys Ser Lys Ser
            20

<210> SEQ ID NO 8
<211> LENGTH: 36
<212> TYPE: PRT
<213> ORGANISM: Bordetella pertussis

<400> SEQUENCE: 8

Phe Gln Thr Arg Gln Asp Asn Leu Ala Gln Val Ile Pro Gly Ser Ser
1               5                   10                  15

Ile Pro Gly Phe Pro Asn Met Gln Ala Ser Arg Ala Ala Ser Gly Ala
                20                  25                  30

Lys Val Glu Gly
        35

<210> SEQ ID NO 9
<211> LENGTH: 19
<212> TYPE: PRT
<213> ORGANISM: Bordetella pertussis

<400> SEQUENCE: 9

Phe Thr Thr Lys Asp Ala Ser Gly Asn Pro Ile Asn Thr Asn His Pro
1               5                   10                  15

Arg Ser Leu

<210> SEQ ID NO 10
<211> LENGTH: 22
<212> TYPE: PRT
<213> ORGANISM: Bordetella pertussis

<400> SEQUENCE: 10

Gln Ser Arg Met Tyr Gln Ala Ala Ala Ser Pro Arg Gly Asn Val Glu
1               5                   10                  15
```

Val Glu Gln Asp Ser Tyr
            20

<210> SEQ ID NO 11
<211> LENGTH: 11
<212> TYPE: PRT
<213> ORGANISM: Bordetella pertussis

<400> SEQUENCE: 11

Asn Asn Leu Phe Asp Lys Lys Tyr Tyr Asp Gln
1               5                   10

<210> SEQ ID NO 12
<211> LENGTH: 43
<212> TYPE: PRT
<213> ORGANISM: Bordetella pertussis

<400> SEQUENCE: 12

His Asp Asp Thr Ser Trp Leu Leu Gln Ala Gly Thr Arg Asn Gly His
1               5                   10                  15

Asp Leu Asp Asn Arg Ala Asp Thr Gly Gly Tyr Gly Ser Lys Arg Ser
            20                  25                  30

Gln Pro Ser Pro Glu Asp Tyr Ala Gln Asn Asn
        35                  40

<210> SEQ ID NO 13
<211> LENGTH: 30
<212> TYPE: PRT
<213> ORGANISM: Bordetella pertussis

<400> SEQUENCE: 13

Phe Lys Arg Arg Ala Asp Leu Asp Gln Met Tyr Gln Gln Gly Ala Gly
1               5                   10                  15

Thr Ser Tyr Gln Tyr Gly Ala Asn Arg Thr His Glu Glu Thr
            20                  25                  30

<210> SEQ ID NO 14
<211> LENGTH: 46
<212> TYPE: PRT
<213> ORGANISM: Bordetella pertussis

<400> SEQUENCE: 14

Gln Arg Leu Arg Leu Asp Ser Ser Gln Asp Ala Arg Arg Thr Arg Asp
1               5                   10                  15

Gly Arg Ala Tyr Ala Arg Pro Gly Asp Pro Tyr Phe Tyr Gly Tyr Pro
            20                  25                  30

Ser Gly Pro Tyr Gly Arg Ser Asn Ser Ile Gln Glu Ser Ile
        35                  40                  45

<210> SEQ ID NO 15
<211> LENGTH: 48
<212> TYPE: PRT
<213> ORGANISM: Bordetella pertussis

<400> SEQUENCE: 15

Tyr Gly Asn Arg Thr Glu Gln Tyr Ser Asp Gly Tyr Asp Asn Cys Pro
1               5                   10                  15

Ala Ile Pro Pro Gly Thr Pro Ala Pro Met Gly Pro Arg Leu Cys Asp
            20                  25                  30

Met Leu His Thr Asn Gln Ala Asp Met Pro Arg Val Lys Gly Ser Gln
        35                  40                  45

<210> SEQ ID NO 16
<211> LENGTH: 28
<212> TYPE: PRT
<213> ORGANISM: Bordetella pertussis

<400> SEQUENCE: 16

Tyr Glu Gln Lys Pro Gln Gln Gly Gly Gly Tyr Gln Asn Asn Pro Asn
1               5                   10                  15

Ala Gly Ala Leu Pro Pro Ser Ser Ser Gly Gly Arg
            20                  25

<210> SEQ ID NO 17
<211> LENGTH: 33
<212> TYPE: PRT
<213> ORGANISM: Bordetella pertussis

<400> SEQUENCE: 17

Arg Ala Pro Ser Ala Thr Glu Leu Tyr Thr Asn Tyr Gly Pro Gly
1               5                   10                  15

Thr Tyr Leu Arg Val Gly Asn Pro Ser Leu Lys Pro Glu Thr Ser Lys
            20                  25                  30

Gly

<210> SEQ ID NO 18
<211> LENGTH: 13
<212> TYPE: PRT
<213> ORGANISM: Bordetella pertussis

<400> SEQUENCE: 18

Asn Arg Tyr Gln Asn Phe Ile Asp Lys Asn Val Pro Leu
1               5                   10

<210> SEQ ID NO 19
<211> LENGTH: 11
<212> TYPE: PRT
<213> ORGANISM: Bordetella pertussis

<400> SEQUENCE: 19

Thr Gly Leu Ala Asn Arg Ala Arg Val Arg Ile
1               5                   10

<210> SEQ ID NO 20
<211> LENGTH: 17
<212> TYPE: PRT
<213> ORGANISM: Bordetella pertussis

<400> SEQUENCE: 20

Ala Val Gly Lys Asp Glu Asn Thr Gly Gln His Leu Asn Ser Val Pro
1               5                   10                  15

Pro

<210> SEQ ID NO 21
<211> LENGTH: 24
<212> TYPE: PRT
<213> ORGANISM: Bordetella pertussis

<400> SEQUENCE: 21

Arg Arg Asp Asp Val Gln Tyr Pro Glu Ala Ser Ala Ser Ala Arg Tyr
1               5                   10                  15

Ala Asp Phe Gln Ala Pro Gly Tyr
            20

<210> SEQ ID NO 22
<211> LENGTH: 31
<212> TYPE: PRT
<213> ORGANISM: Bordetella pertussis

<400> SEQUENCE: 22

Asp Lys Lys Tyr Trp Glu Ala Ile Asn Val Pro Thr Ala Gly Ala Ile
1 5 10 15

Ala Ile Pro Arg Pro Leu Asp Trp Tyr Asn Glu Pro Gly Arg Ser
20 25 30

<210> SEQ ID NO 23
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 23
tacgtgccgg acagggttt 19

<210> SEQ ID NO 24
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 24
attccgacca gcgaagtgaa g 21

<210> SEQ ID NO 25
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 25
atgtccaagt tttcataccc tgc 23

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
tcaggggtag acgacggaaa 20

<210> SEQ ID NO 27
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 27
gctctagaac tagtggatcc ccctacgtgc cggacagggt tt 42

<210> SEQ ID NO 28
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 28
cttcacttcg ctggtcggaa tatgtccaag ttttcatacc ctgc 44

<210> SEQ ID NO 29
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 29
tttccgtcgt ctacccctga gggctgcagg aattcgatat ca 42

<210> SEQ ID NO 30
<211> LENGTH: 16
<212> TYPE: PRT
<213> ORGANISM: Bordetella pertussis

<400> SEQUENCE: 30

Pro Phe Asp Ile Lys Leu Lys Glu Cys Pro Gln Ala Leu Gly Ala Leu
1 5 10 15

<210> SEQ ID NO 31
<211> LENGTH: 13
<212> TYPE: PRT
<213> ORGANISM: Bordetella pertussis

<400> SEQUENCE: 31

Ser Ala Thr Lys Ala Lys Gly Val Glu Phe Arg Leu Ala
1 5 10

<210> SEQ ID NO 32
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 32
cccttcgaca tcaagctgaa gctggacagc tcgcaggac 39

<210> SEQ ID NO 33
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 33
gggctcgaaa tacagcttga gcgattcctg gatcgagttg ct 42

<210> SEQ ID NO 34
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 34
ggcaacctga gcaccgtgtc gctggacagc tcgcaggac 39

<210> SEQ ID NO 35

```
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 35
gatgtgctgg ccgttgaggt tcgattcctg gatcgagttg ct                          42

<210> SEQ ID NO 36
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 36
cccttcgaca tcaagctgaa ggagcagtac tcggacggct a                           41

<210> SEQ ID NO 37
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 37
gggctcgaaa tacagcttga gctggctgcc cttgacccg                              39

<210> SEQ ID NO 38
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 38
ggcaacctga gcaccgtgtc ggagcagtac tcggacggct a                           41

<210> SEQ ID NO 39
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 39
gatgtgctgg ccgttgaggt tctggctgcc cttgacccg                              39

<210> SEQ ID NO 40
<211> LENGTH: 195
<212> TYPE: DNA
<213> ORGANISM: Bordetella pertussis

<400> SEQUENCE: 40
tacgtgccgg acagggtttg atggtttgac taagaaattt cctacaagtc ttgtataaat     60
atccattgat ggacgggatc attactgact gacgaagtgc tgaggtttat ccagactatg    120
gcactggatt tcaaaaccta aaacgagcag gccgataacg gattctgccg attacttcac    180
ttcgctggtc ggaat                                                     195

<210> SEQ ID NO 41
<211> LENGTH: 615
<212> TYPE: DNA
<213> ORGANISM: Bordetella pertussis
```

<400> SEQUENCE: 41

```
atgtccaagt tttcataccc tgccttgcgc gccgcgctta tccttgccgc ctcgcccgta      60
ctgccagcgc tggccaacga cggcaccatc gtcatcaccg gcagcatctc cgaccagacc     120
tgcgtcatcg aagagcccag caccctcaac catatcaagg tcgtgcaact gcccaagatt     180
tccaagaacg cgctcaggaa cgacggcgac accgccggcg ccacgccctt cgacatcaag     240
ctgaaggaat gccccaggc gctgggcgcg ctcaagctgt atttcgagcc ggcatcacc      300
accaactacg acacgggcga tctgattgcc tacaagcaga cctacaacgc atccggcaac     360
ggcaacctga gcaccgtgtc gtccgccacc aaggccaagg gcgtggagtt cgcctggcc      420
aacctcaacg gccagcacat ccgcatgggc acggacaaaa ccacgcaagc cgcgcaaacc     480
tttaccggca aggtcaccaa tggcagcaag agctacaccc tgcgctatct cgcctcgtac     540
gtgaagaaac ccaaggaaga tgtcgacgcg gcccagatca ccagctacgt cggcttttcc     600
gtcgtctacc cctga                                                      615
```

<210> SEQ ID NO 42
<211> LENGTH: 204
<212> TYPE: PRT
<213> ORGANISM: Bordetella pertussis

<400> SEQUENCE: 42

```
Met Ser Lys Phe Ser Tyr Pro Ala Leu Arg Ala Ala Leu Ile Leu Ala
1               5                   10                  15

Ala Ser Pro Val Leu Pro Ala Leu Ala Asn Asp Gly Thr Ile Val Ile
            20                  25                  30

Thr Gly Ser Ile Ser Asp Gln Thr Cys Val Ile Glu Glu Pro Ser Thr
        35                  40                  45

Leu Asn His Ile Lys Val Val Gln Leu Pro Lys Ile Ser Lys Asn Ala
    50                  55                  60

Leu Arg Asn Asp Gly Asp Thr Ala Gly Ala Thr Pro Phe Asp Ile Lys
65                  70                  75                  80

Leu Lys Glu Cys Pro Gln Ala Leu Gly Ala Leu Lys Leu Tyr Phe Glu
                85                  90                  95

Pro Gly Ile Thr Thr Asn Tyr Asp Thr Gly Asp Leu Ile Ala Tyr Lys
            100                 105                 110

Gln Thr Tyr Asn Ala Ser Gly Asn Gly Asn Leu Ser Thr Val Ser Ser
        115                 120                 125

Ala Thr Lys Ala Lys Gly Val Glu Phe Arg Leu Ala Asn Leu Asn Gly
    130                 135                 140

Gln His Ile Arg Met Gly Thr Asp Lys Thr Thr Gln Ala Ala Gln Thr
145                 150                 155                 160

Phe Thr Gly Lys Val Thr Asn Gly Ser Lys Ser Tyr Thr Leu Arg Tyr
                165                 170                 175

Leu Ala Ser Tyr Val Lys Lys Pro Lys Glu Asp Val Asp Ala Ala Gln
            180                 185                 190

Ile Thr Ser Tyr Val Gly Phe Ser Val Val Tyr Pro
        195                 200
```

<210> SEQ ID NO 43
<211> LENGTH: 23
<212> TYPE: PRT
<213> ORGANISM: Bordetella pertussis

<400> SEQUENCE: 43

```
Asp Thr Glu Asp Val Lys Ile Val Leu Asp Gly Ala Pro Lys Gly Phe
1               5                   10                  15

Glu Lys Tyr Arg Gln Gly Ser
            20

<210> SEQ ID NO 44
<211> LENGTH: 76
<212> TYPE: PRT
<213> ORGANISM: Bordetella pertussis

<400> SEQUENCE: 44

Asp Thr Lys Asp Ala Ala Asp Leu Leu Pro Pro Gly Ala Arg Phe Gly
1               5                   10                  15

Ala Leu Ala Lys Tyr Gly Arg His Ser Asn Asp Gly Gln Asp Ile Tyr
            20                  25                  30

Ser Val Ala Leu Tyr Gly Arg Thr Arg Ala Asp Gly Ala Asp Gly Leu
        35                  40                  45

Leu Tyr Ala Asn Arg Arg Asp Gly Gly Asp Leu Arg Arg Pro Asp Gly
    50                  55                  60

Thr Arg Phe Ala Tyr Ser Arg Asn Asn Gln Arg Ser
65                  70                  75

<210> SEQ ID NO 45
<211> LENGTH: 38
<212> TYPE: PRT
<213> ORGANISM: Bordetella pertussis

<400> SEQUENCE: 45

Ser Asn Ala Ala Gly Trp Gln Pro Phe Ala Lys Arg Asp Asp Leu
1               5                   10                  15

Pro Ala Pro Ser Gln Ala Asp Ile Asp Arg Tyr Gly Leu Thr Glu Ala
            20                  25                  30

Trp Arg Arg Lys Leu Val
            35

<210> SEQ ID NO 46
<211> LENGTH: 99
<212> TYPE: PRT
<213> ORGANISM: Bordetella pertussis

<400> SEQUENCE: 46

Ala Arg Ser Asp Thr Arg Gln Arg Asp Arg Arg Ser Ser Arg Ala Ser
1               5                   10                  15

Gln Ser Ala Phe Leu Gly Thr Leu Gly Asn Lys Ser Trp Val Asp Tyr
            20                  25                  30

Arg Asp Asp Arg Phe Asp Leu Ser Asn Glu Ser His Val Ala Leu Gly
        35                  40                  45

Thr Ala Glu His Val Leu Leu Ala Gly Leu Arg Trp His Arg His Arg
    50                  55                  60

Arg Asp Thr Leu Met Tyr Tyr Pro Pro Gly Arg Gly Glu Pro Asp Tyr
65                  70                  75                  80

Asn His Gly Tyr Phe Gln Pro His Tyr Met Pro Ser Gly Thr Gln Thr
                85                  90                  95

Val Arg Ser

<210> SEQ ID NO 47
<211> LENGTH: 18
<212> TYPE: PRT
```

<213> ORGANISM: Bordetella pertussis

<400> SEQUENCE: 47

Val Ala Asn Thr Gly Arg Pro Asn Asp Ala Pro Arg Tyr Asn Asn Pro
1               5                   10                  15

Ala Pro

<210> SEQ ID NO 48
<211> LENGTH: 5
<212> TYPE: PRT
<213> ORGANISM: Bordetella pertussis

<400> SEQUENCE: 48

Lys Ala Ala Arg Gly
1               5

<210> SEQ ID NO 49
<211> LENGTH: 17
<212> TYPE: PRT
<213> ORGANISM: Bordetella pertussis

<400> SEQUENCE: 49

Ala Lys Ser Asn Val Ser Gly Ser Ser Arg Ala Leu Arg Pro Glu Arg
1               5                   10                  15

Ile

<210> SEQ ID NO 50
<211> LENGTH: 42
<212> TYPE: PRT
<213> ORGANISM: Bordetella pertussis

<400> SEQUENCE: 50

Phe Arg Asn Arg Gly Lys His Glu Ile Phe Gln Arg Arg Gly Val Ala
1               5                   10                  15

Cys Arg Gly Gln Ala Glu Gly Gly Ala Ala Ser Asp Cys Pro Lys Pro
            20                  25                  30

Leu Ser Asn Tyr Arg Asn Leu Pro Gly Tyr
        35                  40

<210> SEQ ID NO 51
<211> LENGTH: 20
<212> TYPE: PRT
<213> ORGANISM: Bordetella pertussis

<400> SEQUENCE: 51

Arg Asp Ala Ser Pro Arg Asp Pro Trp Gly Pro Arg Thr Trp Ile Ala
1               5                   10                  15

Glu Ile Pro Pro
            20

<210> SEQ ID NO 52
<211> LENGTH: 26
<212> TYPE: PRT
<213> ORGANISM: Bordetella pertussis

<400> SEQUENCE: 52

Val Arg Arg Gln Asp Arg Ser Pro Thr Asp Gly Asp Pro Leu Ala Gly
1               5                   10                  15

Tyr Trp Ala Leu Pro Lys Thr Ala Gly Tyr
            20                  25

<210> SEQ ID NO 53
<211> LENGTH: 22
<212> TYPE: PRT
<213> ORGANISM: Bordetella pertussis

<400> SEQUENCE: 53

Asp Asn Leu Phe Asn Arg Pro Tyr His Pro Tyr Leu Gly Glu Ala Val
1               5                   10                  15

Ser Gly Thr Gly Arg Asn
            20

<210> SEQ ID NO 54
<211> LENGTH: 13
<212> TYPE: PRT
<213> ORGANISM: Bordetella pertussis

<400> SEQUENCE: 54

Tyr Thr Asn Gln Pro Glu Asp Ser Arg Glu Gly Asn Thr
1               5                   10

<210> SEQ ID NO 55
<211> LENGTH: 33
<212> TYPE: PRT
<213> ORGANISM: Bordetella pertussis

<400> SEQUENCE: 55

Asn Lys Thr Asn Pro Asp Ala Arg Asp Ile Asn Ala Gly His Ala Asn
1               5                   10                  15

Thr Ser Asp Asn Gly Asn Pro Ser Thr Ala Gly Arg Glu Gly Val Ile
            20                  25                  30

Asn

<210> SEQ ID NO 56
<211> LENGTH: 33
<212> TYPE: PRT
<213> ORGANISM: Bordetella pertussis

<400> SEQUENCE: 56

Gln Gly Asn Leu Phe Ala Gly Asp Thr Met Asn Asn Ala Asn Ser Asp
1               5                   10                  15

Phe Ser Asp Ser Leu Tyr Gly Lys Glu Thr Asn Ala Met Tyr Arg Glu
            20                  25                  30

Asn

<210> SEQ ID NO 57
<211> LENGTH: 30
<212> TYPE: PRT
<213> ORGANISM: Bordetella pertussis

<400> SEQUENCE: 57

Thr Arg Asn Ala Arg Gln Arg Glu Gly Leu Ala Gly Gly Pro Glu Gly
1               5                   10                  15

Ala Pro Thr Ala Gly Gly Tyr Asp Thr Ala Arg Leu Lys Asn
            20                  25                  30

<210> SEQ ID NO 58
<211> LENGTH: 36
<212> TYPE: PRT
<213> ORGANISM: Bordetella pertussis

<400> SEQUENCE: 58

Leu Arg Glu Ser Leu Glu Asp Pro Ala Gly Thr Arg Gln Thr Tyr Thr

```
                1               5                  10                  15
Gly Gly Ala Ile Gly Gly Thr Ala Pro Ala Asp Arg Asp Pro Lys Ser
                20                  25                  30

Arg Gln Thr Ser
        35

<210> SEQ ID NO 59
<211> LENGTH: 7
<212> TYPE: PRT
<213> ORGANISM: Bordetella pertussis

<400> SEQUENCE: 59

Asn Ser Glu Phe Gly Ser Asn
1               5

<210> SEQ ID NO 60
<211> LENGTH: 42
<212> TYPE: PRT
<213> ORGANISM: Bordetella pertussis

<400> SEQUENCE: 60

Lys Ala Pro Asn Leu Tyr Gln Ser Asn Pro Asn Tyr Leu Leu Tyr Ser
1               5                   10                  15

Arg Gly Asn Gly Cys Leu Ala Ser Gln Thr Asn Thr Asn Gly Cys Tyr
                20                  25                  30

Leu Val Gly Asn Glu Asp Leu Ser Pro Glu
            35                  40

<210> SEQ ID NO 61
<211> LENGTH: 38
<212> TYPE: PRT
<213> ORGANISM: Bordetella pertussis

<400> SEQUENCE: 61

Phe Arg Asn Asp Tyr Arg Asn Lys Ile Val Ala Gly Thr Asp Val Gln
1               5                   10                  15

Tyr Arg Leu Ala Asn Gly Ala Arg Val Leu Gln Trp Thr Asn Ser Gly
                20                  25                  30

Lys Ala Val Val Glu Gly
            35

<210> SEQ ID NO 62
<211> LENGTH: 14
<212> TYPE: PRT
<213> ORGANISM: Bordetella pertussis

<400> SEQUENCE: 62

Lys Glu Lys Ala Thr Gly Glu Pro Leu Ser Val Ile Pro Glu
1               5                   10

<210> SEQ ID NO 63
<211> LENGTH: 24
<212> TYPE: PRT
<213> ORGANISM: Bordetella pertussis

<400> SEQUENCE: 63

Tyr Gly Lys Gln Glu Gly Pro Ser Thr Asn Val Arg Thr Gly Val Glu
1               5                   10                  15

Leu Asn Gly Asp Gly Arg Gln Thr
            20
```

<210> SEQ ID NO 64
<211> LENGTH: 24
<212> TYPE: PRT
<213> ORGANISM: Bordetella pertussis

<400> SEQUENCE: 64

Asp Lys Gln Leu Tyr Arg Glu Gly Asn Ala Ser Ser Ala Gly Ala Ala
1               5                   10                  15
Thr Tyr Asn Glu Pro Gly Arg Ala
            20

<210> SEQ ID NO 65
<211> LENGTH: 25
<212> TYPE: PRT
<213> ORGANISM: Bordetella pertussis

<400> SEQUENCE: 65

Leu Lys Arg Arg Ser Ser Asp Tyr Arg Val Pro Asp Trp Pro Asp Gly
1               5                   10                  15
Lys Leu Ala Gly Ser Tyr Ser Glu Ser
            20                  25

<210> SEQ ID NO 66
<211> LENGTH: 66
<212> TYPE: PRT
<213> ORGANISM: Bordetella pertussis

<400> SEQUENCE: 66

Leu Glu Ser Lys Tyr Gly Leu Pro Gly His Asn His Glu Tyr Glu Gly
1               5                   10                  15
Cys His Pro His Gly Ser His Leu His Cys Gly Gly His Asp Asp His
            20                  25                  30
Gly His Gly His Asp Glu His Glu Gly Glu Ala Gly His Asp His
        35                  40                  45
Gly His Glu His Gly Ala Gly Asp Val Pro Tyr Val Lys Leu Arg Ser
    50                  55                  60
Asn Arg
65

<210> SEQ ID NO 67
<211> LENGTH: 21
<212> TYPE: PRT
<213> ORGANISM: Bordetella pertussis

<400> SEQUENCE: 67

Thr Asp Tyr Arg His Asp Glu Ile Glu Gly Gly Gln Leu Gly Thr Arg
1               5                   10                  15
Phe Gln Asn Arg Gly
            20

<210> SEQ ID NO 68
<211> LENGTH: 19
<212> TYPE: PRT
<213> ORGANISM: Bordetella pertussis

<400> SEQUENCE: 68

Ser Asp Phe Arg Ala Thr Gly Glu Glu Ala Phe Leu Pro Arg Ser Lys
1               5                   10                  15
Thr Arg Ala

<210> SEQ ID NO 69

```
<211> LENGTH: 16
<212> TYPE: PRT
<213> ORGANISM: Bordetella pertussis

<400> SEQUENCE: 69

Gln Arg Val Ser Pro Gln Ser Gly Ala Pro Ala Ser Arg Thr Ala Gly
1               5                   10                  15

<210> SEQ ID NO 70
<211> LENGTH: 32
<212> TYPE: PRT
<213> ORGANISM: Bordetella pertussis

<400> SEQUENCE: 70

Arg Leu Pro Ser Ala Gln Glu Leu Tyr Ala Asp Gly Val His Leu Ala
1               5                   10                  15

Thr Asn Thr Tyr Glu Ile Gly Asp Pro Gly Leu Asp Arg Glu Thr Ser
                20                  25                  30

<210> SEQ ID NO 71
<211> LENGTH: 30
<212> TYPE: PRT
<213> ORGANISM: Bordetella pertussis

<400> SEQUENCE: 71

Asn Arg Val Lys Asn Tyr Ile Tyr Ala Asn Thr Leu Asp Arg Tyr Glu
1               5                   10                  15

Asp Phe Arg Leu Ile Glu Tyr Thr Gln Arg Asp Ala Glu Phe
                20                  25                  30

<210> SEQ ID NO 72
<211> LENGTH: 17
<212> TYPE: PRT
<213> ORGANISM: Bordetella pertussis

<400> SEQUENCE: 72

Val Arg Gly Arg Leu Thr Gly Gly Gly Asn Leu Pro Arg Ile Pro
1               5                   10                  15

Ala

<210> SEQ ID NO 73
<211> LENGTH: 19
<212> TYPE: PRT
<213> ORGANISM: Bordetella pertussis

<400> SEQUENCE: 73

Val Tyr Arg Gln Asp Asp Ile Ala Ala Tyr Glu Ser Ser Thr Pro Gly
1               5                   10                  15

Tyr Asp Met

<210> SEQ ID NO 74
<211> LENGTH: 25
<212> TYPE: PRT
<213> ORGANISM: Bordetella pertussis

<400> SEQUENCE: 74

Asn Asn Leu Leu Asn Lys Leu Ala Phe Asn His Ala Ser Phe Ile Ser
1               5                   10                  15

Thr Val Ala Pro Leu Pro Gly Arg Ser
                20                  25
```